US012465676B2

(12) United States Patent
Doyle

(10) Patent No.: US 12,465,676 B2
(45) Date of Patent: Nov. 11, 2025

(54) DETERMINING A MODALITY OF AN EXTRACORPOREAL BLOOD CIRCUIT

(71) Applicant: Fresenius Medical Care Holdings, Inc., Waltham, MA (US)

(72) Inventor: Matthew J. Doyle, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1135 days.

(21) Appl. No.: 17/369,098

(22) Filed: Jul. 7, 2021

(65) Prior Publication Data

US 2023/0010811 A1 Jan. 12, 2023

(51) Int. Cl.
*A61M 1/36* (2006.01)
*G16H 20/40* (2018.01)

(52) U.S. Cl.
CPC ............ *A61M 1/367* (2013.01); *G16H 20/40* (2018.01); *A61M 2205/276* (2013.01); *A61M 2205/502* (2013.01)

(58) Field of Classification Search
None
See application file for complete search history.

(56) References Cited

U.S. PATENT DOCUMENTS 8,298,167 B2 10/2012 Peters et al.
9,514,322 B2 12/2016 Golshenas
9,750,864 B2 9/2017 Kopperschimdt
10,342,634 B2 7/2019 Daniel
2005/0070837 A1* 3/2005 Ferrarini ............. A61M 60/585 604/4.01
2005/0131332 A1* 6/2005 Kelly .............. A61M 1/362265 604/4.01
2007/0118813 A1 5/2007 Forstall et al.
(Continued)

FOREIGN PATENT DOCUMENTS

EP 3148607 4/2017
WO 2010/062720 A1 6/2010
(Continued)

OTHER PUBLICATIONS

International Preliminary Report on Patentability in International Appln. No. PCT/US2022/034715, mailed Jan. 18, 2024, 8 pages.
(Continued)

*Primary Examiner* — Jonathan M Peo
(74) *Attorney, Agent, or Firm* — Fish & Richardson P.C.

(57) ABSTRACT

This disclosure relates to medical fluid pumping systems and related devices and methods. In some aspects, a blood treatment system includes a user interface; a processor in communication with the user interface and configured to perform operations including: presenting instructions on the user interface, the instructions pertaining to at least one modality of a set of modalities, wherein the set of modalities include hemodialysis (HD), hemofiltration (HF), and hemodiafiltration (HDF), wherein the instructions pertain to a component of a blood treatment machine of the blood treatment system; receiving information associated with the component of the blood treatment machine; and eliminating modalities from the set of modalities to determine a modality of the blood treatment machine based on the received information.

33 Claims, 21 Drawing Sheets

(56) References Cited

U.S. PATENT DOCUMENTS

| | | | | |
|---|---|---|---|---|
| 2014/0216250 | A1 | 8/2014 | Meyer et al. | |
| 2017/0172695 | A1* | 6/2017 | Daniel .................... | A61M 1/16 |
| 2018/0117296 | A1 | 5/2018 | Damiano et al. | |
| 2019/0198152 | A1 | 6/2019 | Hakansson et al. | |
| 2019/0328950 | A1* | 10/2019 | Nilsson ............... | A61M 1/3431 |

FOREIGN PATENT DOCUMENTS

| | | | |
|---|---|---|---|
| WO | 2011/144747 | A1 | 11/2011 |
| WO | WO 2014/105755 | | 7/2014 |
| WO | 2017/007968 | A1 | 1/2017 |
| WO | 2018/001993 | A1 | 1/2018 |

OTHER PUBLICATIONS

International Search Report and Written Opinion in International Appln. No. PCT/US2022/034715, mailed Dec. 14, 2022, 13 pages.

* cited by examiner

DETERMINING A MODALITY OF AN EXTRACORPOREAL BLOOD CIRCUIT

TECHNICAL FIELD

This disclosure relates to determining a modality of an extracorporeal blood circuit of a blood treatment system.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a blood treatment machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the blood treatment machine acts as an artificial kidney for cleansing the blood.

SUMMARY

In one aspect, a blood treatment system includes a user interface and a processor in communication with the user interface and configured to perform operations. The operations include presenting instructions on the user interface. The instructions pertain to at least one modality of a set of modalities, wherein the set of modalities include hemodialysis (HD), hemofiltration (HF), and hemodiafiltration (HDF). The instructions pertain to a component of a blood treatment machine of the blood treatment system. The operations include receiving information associated with the component of the blood treatment machine and eliminating modalities from the set of modalities to determine a modality of the blood treatment machine based on the received information.

In a second aspect, a method includes presenting instructions on a user interface of a blood treatment machine. The instructions pertain to at least one modality of a set of modalities, wherein the set of modalities include hemodialysis (HD), hemofiltration (HF), and hemodiafiltration (HDF). The instructions pertain to a component of the blood treatment machine. The method includes receiving information associated with the component of the blood treatment machine. The method includes eliminating modalities, by a processor of the blood treatment machine, from the set of modalities to determine a modality of the blood treatment machine based on the received information.

In a third aspect, a method includes detecting a requested treatment mode change during treatment. The method includes receiving information associated with one or more components of the blood treatment machine. The method includes presenting instructions on a user interface of a blood treatment machine. The instructions pertaining to a desired modality and additionally based on the current modality, wherein the current and desired modalities include hemodialysis (HD), hemofiltration (HF), and hemodiafiltration (HDF). The instructions pertaining to a component of the blood treatment machine. The method includes entering a desired treatment modality of the blood treatment machine based on the received information.

In a fourth aspect, a method includes presenting instructions on a user interface of a blood treatment machine. The instructions pertaining to at least one modality of a set of modalities, wherein the set of modalities include hemodialysis (HD), hemofiltration (HF), and hemodiafiltration (HDF). The instructions pertaining to a component of the blood treatment machine. The method includes receiving information associated with the component of the blood treatment machine. The method includes receiving information that a hemodialysis (HD) treatment modality is not desired. The method includes initiating a pressure test to ensure correct placement of a substitution fluid line based on received information and eliminating modalities, by a processor of the blood treatment machine, from the set of modalities to determine a modality of the blood treatment machine based on the received information.

In a fifth aspect, a method includes detecting a requested disposable fluid line replacement during treatment. The method includes receiving information associated with one or more components of the blood treatment machine. The method includes presenting instructions on a user interface of a blood treatment machine. The instructions pertaining to the replacement of a disposable fluid line. The method includes reentering a treatment modality of the blood treatment machine based on the received information.

In a sixth aspect, a method includes presenting instructions on a user interface of a blood treatment machine. The instructions pertaining to at least one modality of a set of modalities, wherein the set of modalities include hemodialysis (HD), hemofiltration (HF), and hemodiafiltration (HDF). The instructions pertaining to a component of the blood treatment machine. The method includes receiving information associated with the component of the blood treatment machine. The method includes eliminating modalities, by a processor of the blood treatment machine, from the set of modalities. The method includes receiving updated information associated with the component of the blood treatment machine. The method includes re-presenting instructions on a user interface of a blood treatment machine, the instructions pertaining to at least one modality of a set of modalities, wherein the set of modalities include hemodialysis (HD), hemofiltration (HF), and hemodiafiltration (HDF), wherein the instructions pertain to a component of the blood treatment machine. The method includes receiving information associated with the component of the blood treatment machine and re-eliminating modalities, by a processor of the blood treatment machine, from the set of modalities to determine a modality of the blood treatment machine based on the received information.

Implementations can include one or more of the following features.

In some implementations, the instructions are for assisting a user in installing the component on the blood treatment machine.

In some implementations, presenting the instructions on the user interface includes presenting an image representing the component being installed on the blood treatment machine.

In some implementations, receiving the information includes receiving information regarding whether the component is installed on the blood treatment machine.

In some implementations, receiving the information includes receiving information regarding detection of a presence of the component using a sensor of the blood treatment machine.

In some implementations, the received information is associated with at least one of a disposable component of the blood treatment system and a reusable component of the blood treatment system. In some cases, the disposable component is a fluid line and the reusable component is at least one of a substitution fluid pump, a single-needle blood pump, or a combination thereof. In some cases, the disposable component is a dialyzer and the reusable component is at least one of a set of dialysate lines, a dialyzer line shunt, or a combination thereof.

In some implementations, receiving the information includes receiving information regarding whether the component is needed for a particular modality of the set of modalities.

In some implementations, receiving information includes receiving user input via the user interface.

In some implementations, eliminating modalities includes eliminating modalities based on whether the component is installed on the blood treatment machine and whether the component is associated with a particular modality of the set of modalities.

In some implementations, eliminating the modalities includes eliminating single-needle modalities when the component is a single-needle pump and the received information indicates that the single-needle pump is not installed on the blood treatment machine.

In some implementations, eliminating the modalities includes eliminating dual-needle modalities when the component is a single-needle pump and the received information indicates that the single-needle pump is installed with a single-needle fluid line attached to the single-needle pump.

In some implementations, eliminating the modalities includes eliminating single-needle modalities when the component is a single-needle pump and the received information includes an indication that: (i) the single-needle pump is installed on the blood treatment machine and a single-needle fluid line is not attached to the single-needle pump, and/or (ii) a single-needle fluid line is not desired based on user input via the user interface.

In some implementations, eliminating the modalities includes eliminating filtration modalities when the component is a substituate pump and the received information indicates that the substituate pump is not installed on the blood treatment machine.

In some implementations, eliminating the modalities includes eliminating filtration modalities when the component is a substituate pump and the received information comprises an indication that: (i) the substituate pump is installed on the blood treatment machine and a substitution fluid line is not attached to the substituate pump, and/or (ii) use of a substituate fluid pump is not desired based on user input via the user interface.

In some implementations, eliminating the modalities includes eliminating modalities requiring a second dialyzer when the component is a second set of dialysate lines with an associated shunt and the received information indicates that the second set of dialysate lines with the associated shunt is not installed on the blood treatment machine.

In some implementations, eliminating the modalities includes eliminating modalities requiring a second dialyzer when the component is a second set of dialysate lines with an associated shunt and the received information is an indication that: (i) the second set of dialysate lines with the associated shunt is installed on the blood treatment machine and the second set of dialysate lines remain on the associated shunt, and/or (ii) an indication that a second set of dialysate lines is not desired based on user input via the user interface.

In some implementations, eliminating the modalities includes eliminating pre-dilution filtration modalities, post-dilution filtration modalities, mid-dilution filtration modalities, or a combination thereof, and the received information is an indication of a placement of a substitution fluid line based on received user input via the user interface.

In some implementations, eliminating the modalities includes eliminating hemodialysis (HD) modalities and the received information is an indication based on received user input via the user interface.

In some implementations, eliminating the modalities includes eliminating hemodiafiltration (HDF) or hemofiltration (HF) modalities and the received information is an indication based on received user input via the user interface.

In some implementations, the instructions are for assisting a user in installing a component on the blood treatment machine, removing a component on the blood treatment machine, or a combination thereof.

In some implementations, presenting the instructions on the user interface include presenting an image representing the component being installed on the blood treatment machine, removed from the blood treatment machine, or a combination thereof.

In some implementations, receiving the information includes receiving information regarding whether a component or components are installed on the blood treatment machine.

In some implementations, receiving information includes receiving information regarding detection of a presence of a component using a sensor of the blood treatment machine, the absence of a component using a sensor of the blood treatment machine, the detection of a presence of a component using an input received from the user interface of the blood treatment machine, the detection of an absence of a component using an input received from the user interface of the blood treatment machine, or a combination thereof.

In some implementations, the one or more components of the blood treatment machine are a substitution fluid pump, a single-needle blood pump, a secondary set of dialysate lines with a respective shunt, or a combination thereof.

In some implementations, the received information is an indication that a single-needle bloodline is installed on the blood treatment machine, an indication that a single-needle blood pump is not installed on the blood treatment machine, an indication that a single-needle blood pump without a single-needle bloodline is installed on the blood treatment machine, an indication that a substitution fluid line is installed on the blood treatment machine, an indication that a substitution fluid pump is not installed on the blood treatment machine, an indication that a substitution fluid pump without a substitution fluid line is installed on the blood treatment machine, an indication that a second dialyzer is installed on the blood treatment machine, an indication that a second set of dialysate lines with a respective shunt is not installed on the blood treatment machine, an indication that a second set of dialysate lines with a respective shunt without an attached second dialyzer is installed on the blood treatment machine, or a combination thereof.

In some implementations, the system and/or method includes initiating a pressure test to ensure correct placement of a substitution fluid line based on received information.

In some cases, the pressure test includes the introduction of a fluid bolus via a substitution fluid pump and measuring a blood treatment machine parameter.

In some cases, the pressure test includes the introduction of a first fluid bolus via a substitution fluid pump and measuring a blood treatment machine parameter, confirmation of the correct placement of a first substitution fluid line, and the introduction a second fluid bolus via a second substitution fluid pump and measuring a blood treatment machine parameter.

In some cases, the blood treatment machine parameter comprises a venous pressure, a change in venous pressure over time, a difference between a first and second venous pressure, a transmembrane pressure, a change in transmembrane pressure, a difference between a first and second transmembrane pressure, a comparison between a change in venous pressure over time and a transmembrane pressure over time, or a combination thereof.

In some implementations, a rinse connector with a disposable male luer-lock adapter is used for the replacement of a disposable arterial fluid line or a single-needle fluid line.

In some implementations, a disposable female luer-lock to male luer-lock adapter is used for the replacement of a disposable venous fluid line.

In some implementations, a disposable female luer-lock to female luer-lock adapter and male luer-lock cap is used for the replacement of a dialyzer.

In some embodiments, a rinse connector with disposable female luer-lock adapter is used for the priming of a replacement dialyzer.

In some embodiments, a disposable male luer-lock to male luer-lock adapter is used during the replacement of a dialyzer or after the removal of a dialyzer.

In some embodiments, the system primes an arterial fluid line without priming a venous fluid line and/or without priming a dialyzer.

Implementations can include one or more of the following advantages.

Treatment modalities where one or more dialyzers, one or more substitution fluid pumps, and/or single-needle blood pumps are required are appropriately handled by the machine processor such that the user interface guides the user through any combination of potential treatment modalities. Upon entry into treatment, the transitioning between treatment modes and replacement of disposable elements would be achievable through instructions presented on the user interface.

Blood treatment machines described herein include user interfaces with adaptable and interactive setup instructions to present instructions based on the associated components installed on the blood treatment machine to allow users to be guided through setup on only the modality configurations of the blood treatment machine that are available with the end treatment setup being automatically determined as alternatively available treatment setups are iteratively excluded based on the user interaction with the machine. During the setup process, the machine will additionally look for setup changes initiated by the user which would warrant transitioning from one treatment setup to an alternatively available treatment setup. In this way, the blood treatment machines described herein provide instructions to the user in the most efficient manner given the plurality of potential bloodline and machine configurations available on the blood treatment machine to complete setup in the desired treatment modality. Additionally, the display of instructions for modalities that are not possible without installing additional components to the machine or the display of undesired alternatively available treatment setups are avoided, thereby decreasing the time required to for machine setup in the desired treatment modality.

Other aspects, features, and advantages will be apparent from the description and drawings, and from the claims.

DETAILED DESCRIPTION

This disclosure relates generally to extracorporeal blood treatment machines (e.g., dialysis machines). A blood treatment machine can be configured to perform blood treatment according to several different modalities (e.g., hemodialysis (HD), hemofiltration (HF), and hemodiafiltration (HDF), etc.) and a user can be intimidated and confused by the number of possible blood treatment machine configurations to accommodate all these modalities. The blood treatment machines described herein assist a user by presenting instructions that are generated based on the components installed on the blood treatment machine and whether the user intends to perform a particular blood treatment. For example, if a single-needle blood pump is installed, the blood treatment machine can present an inquiry asking the user if a single-needle modality is intended. In response, if the user indicates that a dual-needle blood treatment is intended, the blood treatment machine eliminates single-needle modalities as possible modalities. In turn, as the blood treatment machine progressively eliminates modalities, the dialysis system determines the remaining available modality or modalities and presents interactive user guidance to ensure the user finalizes setup in the desired treatment modality.

Figure 1:
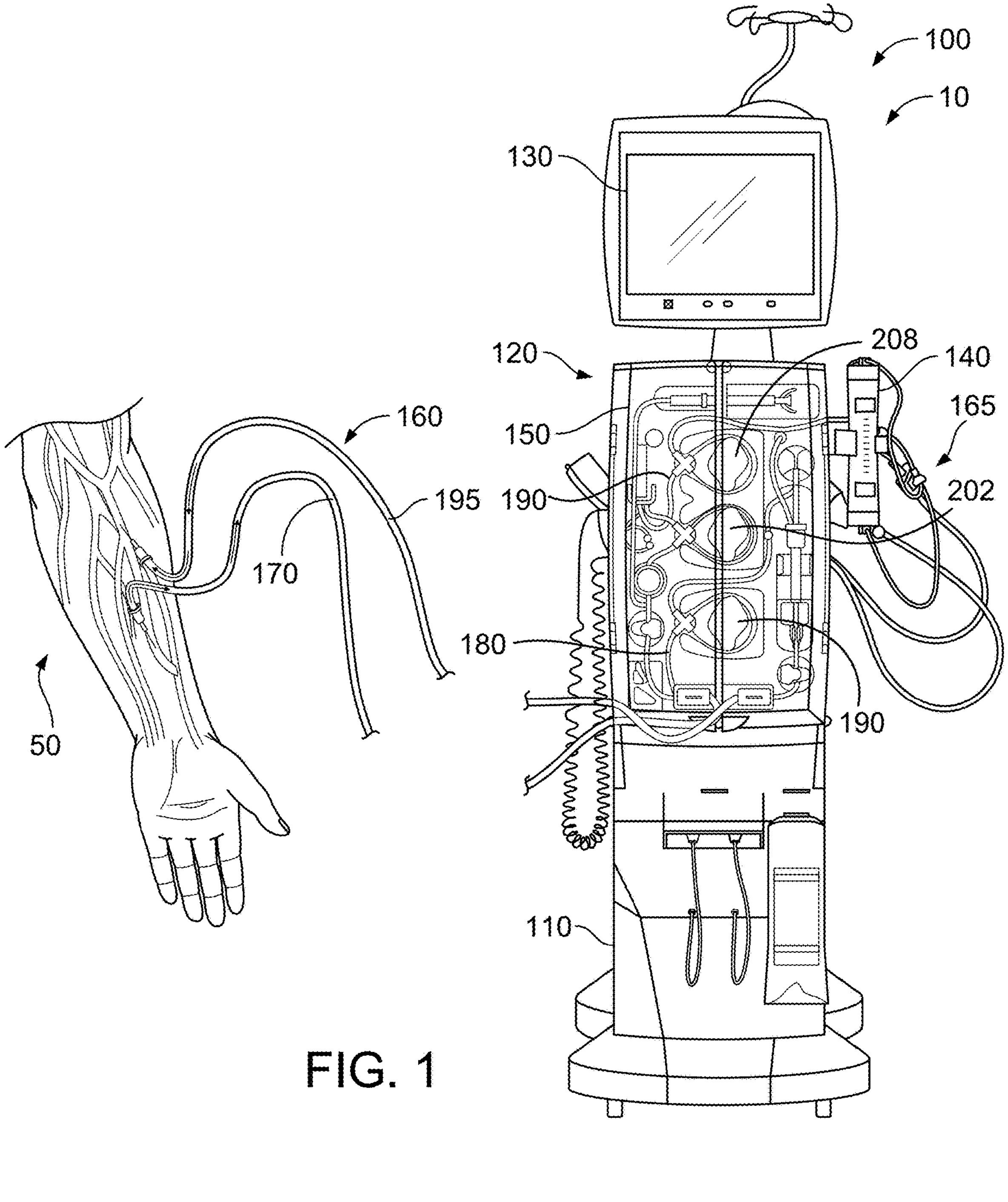
FIG. 1 is a perspective view of a blood treatment machine with disposable tubing installed to perform a single-needle enabled post dilution hemodiafiltration or hemofiltration treatment.

Referring to FIG. 1, a blood treatment system 10 includes a blood treatment machine 100 and a line set 160. The line set 160 includes disposable lines. The line set 160 includes arterial and venous fluid lines 170, 195 connected to a patient 50, as well as other fluid lines and components that are connected to the extracorporeal blood module 120 of the blood treatment machine 100. In the example shown, the line set 160 includes a substitution fluid line 180 and a single-needle blood tubing line 190. The disposable set 160 also includes a dialyzer 140 that is fluidly connected to the arterial and venous fluid lines 170, 195.

The blood treatment machine 100 includes a base 110, an extracorporeal blood module 120, and a user interface 130. The blood treatment machine 100 includes electronic circuitry and a processor in electrical communication with the user interface 130. The user interface 130 can be a color touch screen display. Doors 150 are connected via hinges to the blood treatment machine 100 and enable a user to obtain access to the blood module 120 by opening the doors 150. The doors 150 can be transparent to enable a user to see the blood module 120 through the doors 150 when the doors 150 are in a closed configuration (as shown in FIG. 1).

Still referring to FIG. 1, the arterial fluid line 170, the substitution fluid line 180, the single-needle fluid line 190, and the venous fluid line 195 connect to the extracorporeal blood module 120 of the blood treatment machine 100 and interact with various machine components (this interaction is described in detail below). A dialyzer 140 is fluidly connected to the arterial fluid line 170 and the venous fluid line 195. The dialyzer 140 is additionally in fluid communication with blood treatment machine 100 via dialysate lines 165. In operation, arterial line 170 and venous line 195 are connected to the patient 50 and blood is pumped from the patient 50 using a reusable blood pump 202 (and a reusable single-needle blood pump 208 of the extracorporeal blood module 120 when a single-needle modality is used). In the single-needle and single dialyzer configuration shown in FIGS. 1 and 2, the blood flows through the arterial line 170, the single-needle blood tubing 190, the dialyzer 140, the venous line 195, and then back to the patient 50. As the blood flows through one compartment of the dialyzer 140, dialysate is pumped through an adjacent compartment of the dialyzer and then removed via dialysate lines 165 to clean (e.g., remove toxins from) the blood. Details about the blood treatment process are described with reference to FIGS. 2A and 2B below.

Figure 2A:
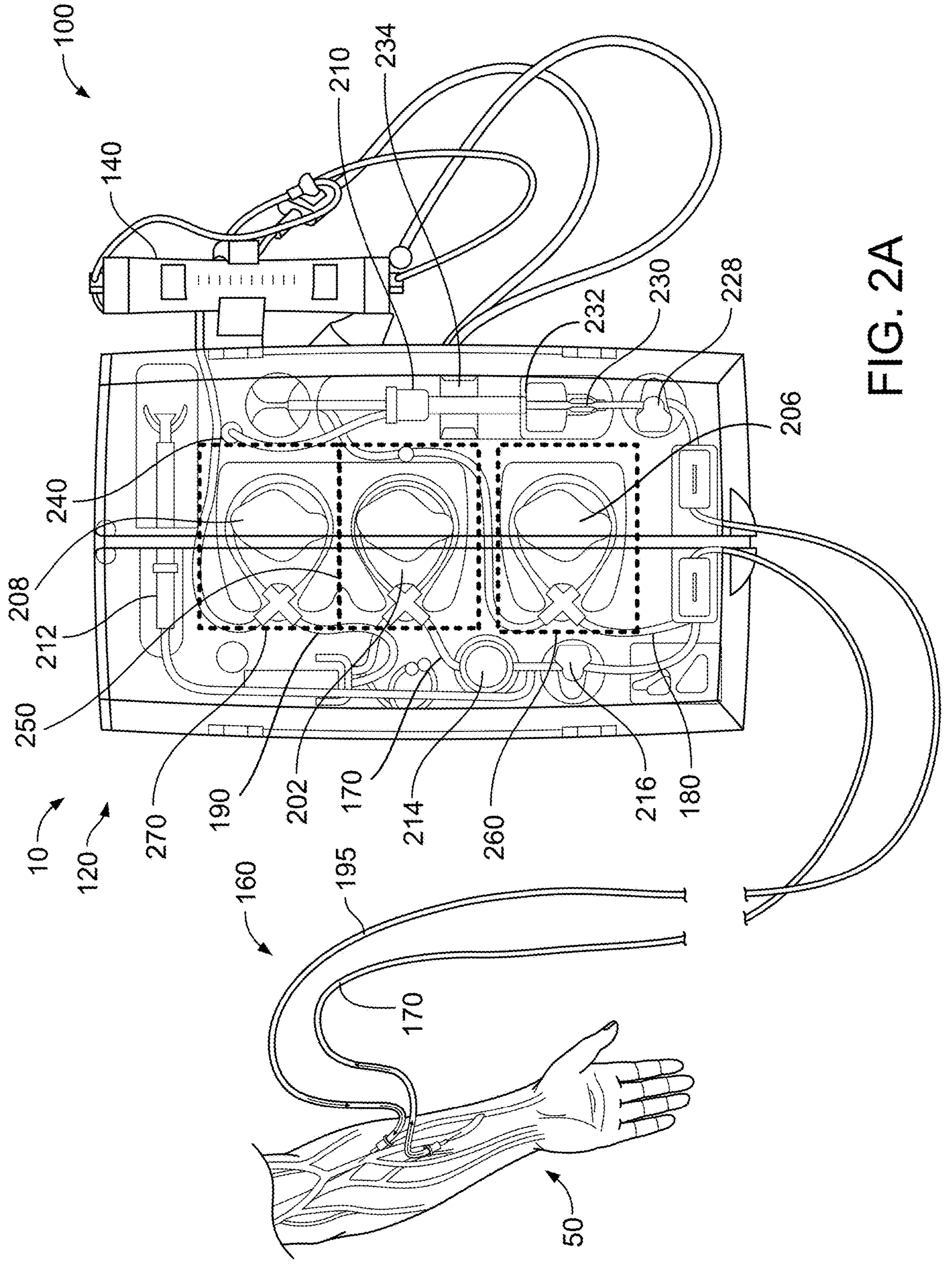
FIG. 2A shows an extracorporeal blood module of the blood treatment machine of FIG. 1.

FIG. 2A shows the extracorporeal blood module 120 of the blood treatment machine 100. The blood pump 202 of the extracorporeal blood module 120 is a peristaltic pump that pumps blood through the arterial fluid line 170 (not shown in FIG. 2A). The blood pump 202 is electrically connected to the processor of the blood treatment machine 100. The extracorporeal blood module 120 includes a sensor 204 (shown in FIG. 2B) that senses when the arterial fluid line 170 is installed into the blood pump 202. The sensor 204 is shown in FIG. 2B based on the boxed region 250 shown in FIG. 2.

Figure 2B:
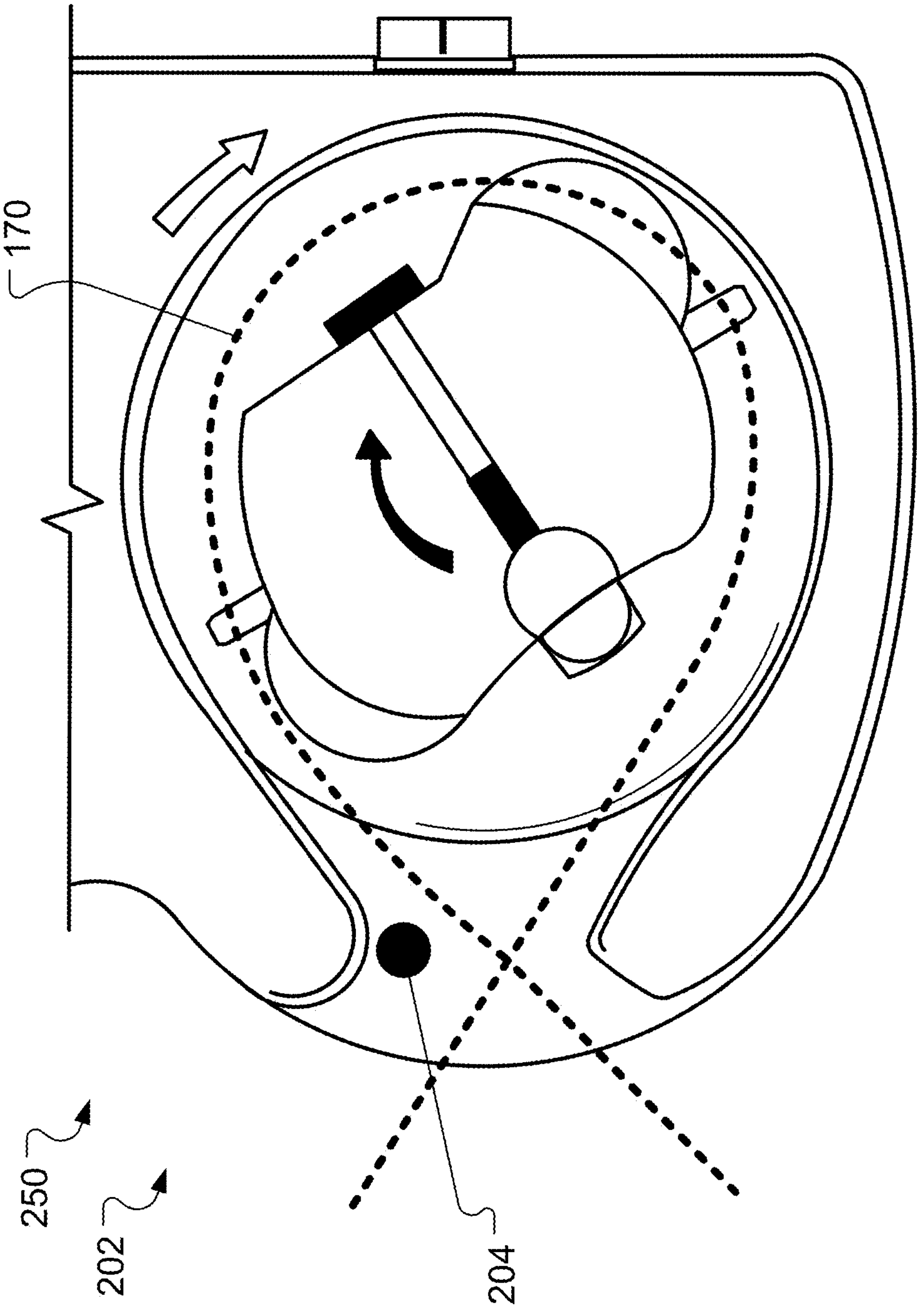
FIG. 2B shows the blood pump of FIG. 2A with an arterial fluid line represented schematically.

FIG. 2B shows a close-up view 250 of the blood pump 202 with the arterial fluid line 170 represented schematically. A recess for a line guide of the blood pump 202 includes the sensor 204. In this way, a signal indicative of whether or not arterial fluid line 170 is installed into the blood pump 202 is generated. This signal can be sent to the processor of the blood treatment machine 100 for processing. In some examples, the blood treatment machine 100 produces an alert (e.g., a sound via a speaker, or an image on the user interface 130) when a line set is installed into the blood pump 202 to indicate to a user that the line set is properly installed into the blood pump 202. Referring back to FIG. 2A, the extracorporeal blood module 120 also includes a reusable substitute pump 206. The substituate pump 206 is substantially similar to the blood pump 202 but is used to pump substitute fluid through the substitution fluid line 180. The substituate pump 206 is electrically connected to the processor of the blood treatment machine 100. The extracorporeal blood module 120 includes a sensor (e.g., similar to sensor 204 of the blood pump 202) that senses when the substitution fluid line 180 is installed into the substituate pump 206.

Figure 2C:
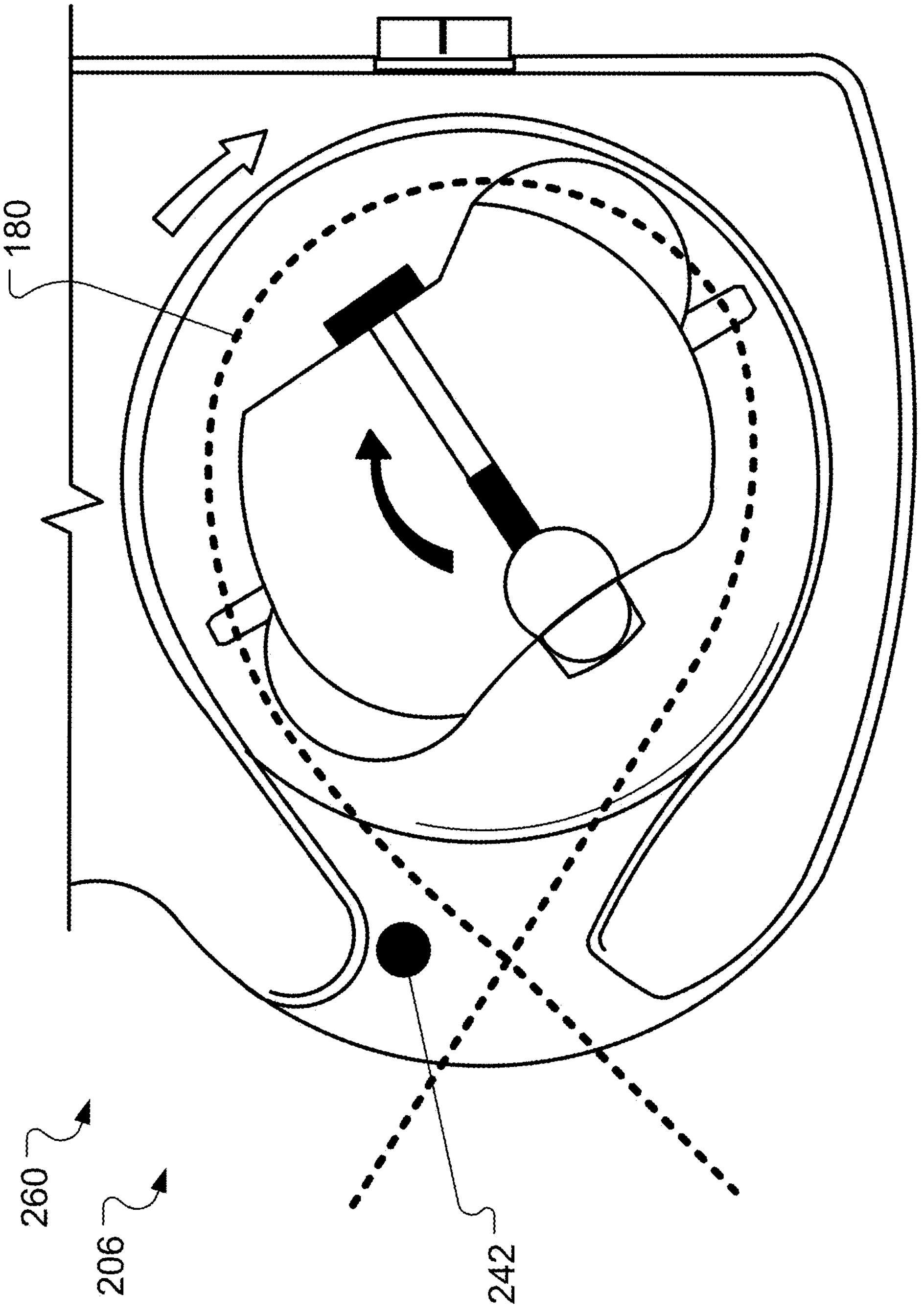
FIG. 2C shows the substitute pump of FIG. 2A with a substitution fluid line represented schematically.

FIG. 2C shows a close-up view 260 of the substituate pump 206 with the substitution fluid line 180 represented schematically. A recess for a line guide of the substituate pump 206 includes a sensor 242. In this way, a signal indicative of whether or not substitution fluid line 180 is installed into the substituate pump 206 is generated. This signal can be sent to the processor of the blood treatment machine 100 for processing. In some examples, the blood treatment machine 100 produces an alert (e.g., a sound via a speaker, or an image on the user interface 130) when a line set is installed into the substituate pump 206 to indicate to a user that the line set is properly installed into the substituate pump 206.

Referring back to FIG. 2A, the substituate fluid line 180 is connected at one end to a substituate source and the other to the venous fluid line 195, indicative of a post-dilution filtration modality. The substitute fluid line 180 is loaded into the substituate pump 206 and the substituate pump 206 is operated to pump the substituate fluid from the substituate port 220 to the venous line during treatment.

The extracorporeal blood module 120 includes a sensor to detect whether the substituate pump 206 is installed on the blood treatment machine 100. If the substituate pump 206 is not installed, the blood treatment machine 100 will not present instructions related to the setup of substitution fluid line 180. Similarly, if the substituate pump 206 is installed, the blood treatment machine 100 can present an inquiry asking the user whether they intend to perform blood treatment (e.g., all "filtration" modalities including pre- and post-filtration) or online priming functionality that uses substitute fluid, or alternatively if they intend to perform blood treatment that does not require substitute fluid (e.g., hemodialysis with saline solution based priming). "Online priming" functionality means that a blood treatment machine can produce substituate on-demand. The machine can, for example, deliver the substituate to the blood circuit via substitution fluid tubing, and the substituate can be used for bloodline preparation (e.g., priming) and/or reinfusion. In this way, the blood treatment machine 100 can eliminate filtration modalities when a substituate pump 206 is not installed on the blood treatment machine 100 (e.g., as determined via the sensors of the blood treatment machine 100) and/or the user confirms via user input on the user interface 130 that substituate will not be used for treatment or priming.

The extracorporeal blood module 120 also includes a reusable single-needle pump 208. The single-needle pump 208 is substantially similar to the blood pump 202 and substituate pump 206 but is used for additional pumping control of blood in single-needle modalities through a single-needle fluid line 190. The single-needle pump 208 is electrically connected to the processor of the blood treatment machine 100. The extracorporeal blood module 120 includes a sensor 244 (e.g., similar to sensor 204 of the blood pump) that senses when a single-needle fluid line 190 is installed into the single-needle pump 208.

Figure 2D:
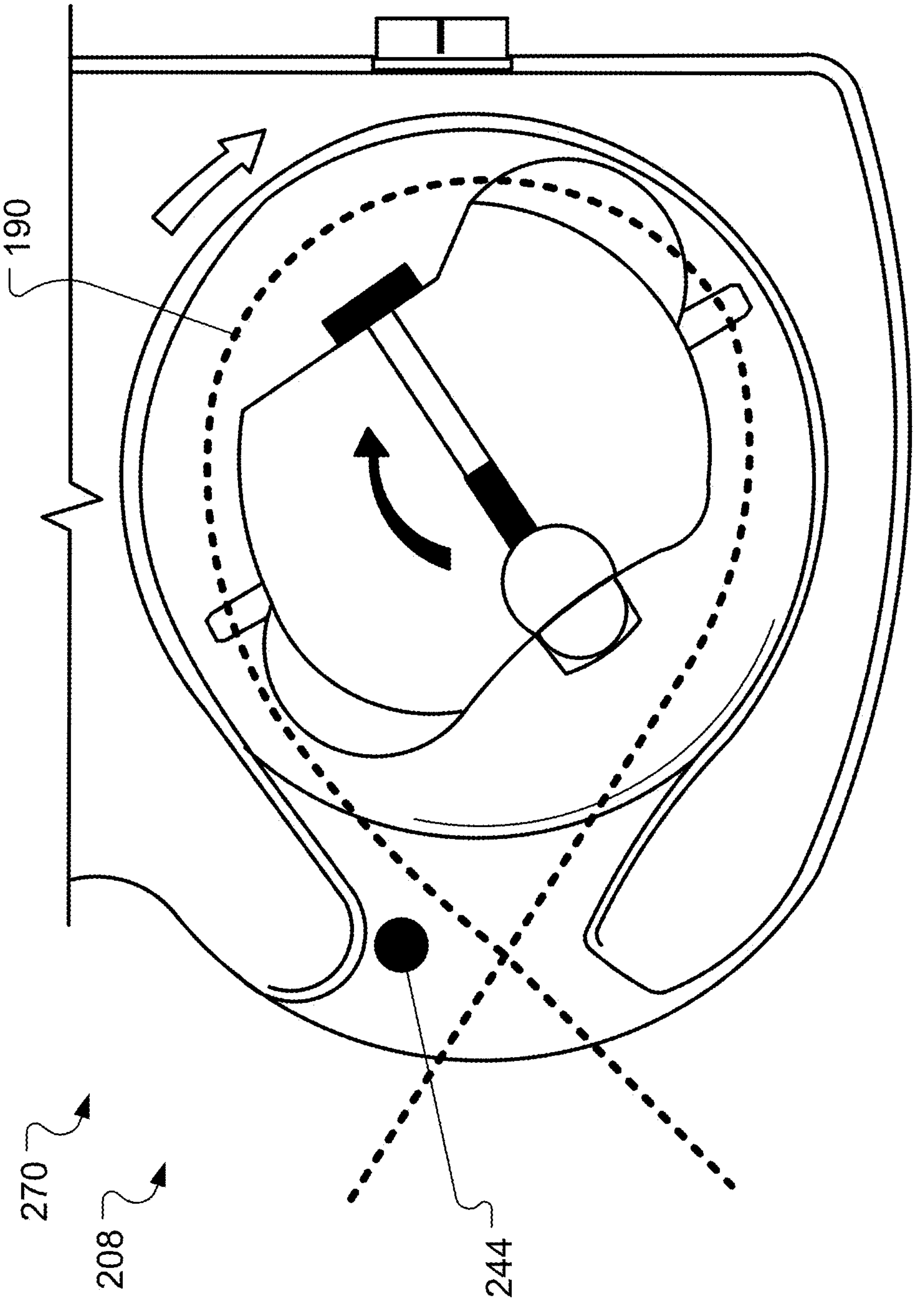
FIG. 2D shows the single-needle pump of FIG. 2A with a single-needle fluid line represented schematically.

FIG. 2D shows a close-up view 270 of the single-needle pump 208 with the single-needle fluid line 190 represented schematically. A recess for a line guide of the single-needle pump 208 includes a sensor 244. In this way, a signal indicative of whether or not a single-needle fluid line 190 is installed into the substituate pump 206 is generated. This signal can be sent to the processor of the blood treatment machine 100 for processing. In some examples, the blood treatment machine 100 produces an alert (e.g., a sound via a speaker, or an image on the user interface 130) when a line set is installed into the single-needle pump 208 to indicate to a user that the line set is properly installed into the single-needle pump 208.

In some examples, the extracorporeal blood module 120 includes a sensor to detect whether the single-needle pump 208 is installed on the blood treatment machine 100. For example, if the single-needle pump 208 is not installed, the blood treatment machine 100 will not present instructions that require a single-needle pump 208. Similarly, if the single-needle pump 208 is installed, the blood treatment machine 100 can present an inquiry prompting the user to install a single-needle fluid line if the user intends to use a single-needle pump during the treatment. In this way, the blood treatment machine 100 can eliminate single-needle modalities when a single-needle pump 208 is not installed on the blood treatment machine 100 and/or when the user indicates that a single-needle treatment is not to be carried out.

Referring back to FIG. 2A, the extracorporeal blood module 120 includes a heparin syringe 212, an arterial pressure measurement unit 214, an arterial occlusion clamp 216, a venous occlusion clamp 228, a venous monitoring function 230 (e.g., an optical detector, an air bubble detector, etc.), a locator 232 for venous a bubble catcher, a venous monitoring function 234 (e.g., a level detector, etc.), and a venous pressure port 240.

In the example shown, the venous monitoring function 230 is an air bubble detector and includes a sensor to detect when the venous fluid line 195 is attached to the air bubble detector 230. The sensor is in electrical communication with the processor of the blood treatment machine 100. The blood treatment machine 100 receives this detection information from the sensor and presents a warning during priming if the venous fluid line 195 is not attached to the air bubble detector 230.

The arterial pressure measurement unit 214 and the venous pressure port are in electrical communication with the processor of the blood treatment machine 100 and measure pressure information. For example, the blood treatment machine 100 can determine when the arterial fluid line 170 is properly connected to the arterial occlusion clamp 216 based on the pressure information from the arterial pressure measurement unit 214 during priming. Similarly, the blood treatment machine 100 can determine when the venous fluid line 195 is properly connected to the venous occlusion clamp 228 based on the pressure information from the pressure information from venous pressure port 240 during priming. Additionally, the blood treatment machine 100 can initiate a heparin test upon installation of the heparin syringe 212. For example, the blood treatment machine 100 can use a result of the heparin test to determine whether the injection of heparin can be detected through changes in arterial pressure. In the example shown, heparin is injected from the syringe 212 into the fluid line 170 before the blood pump 202.

Figure 3A:
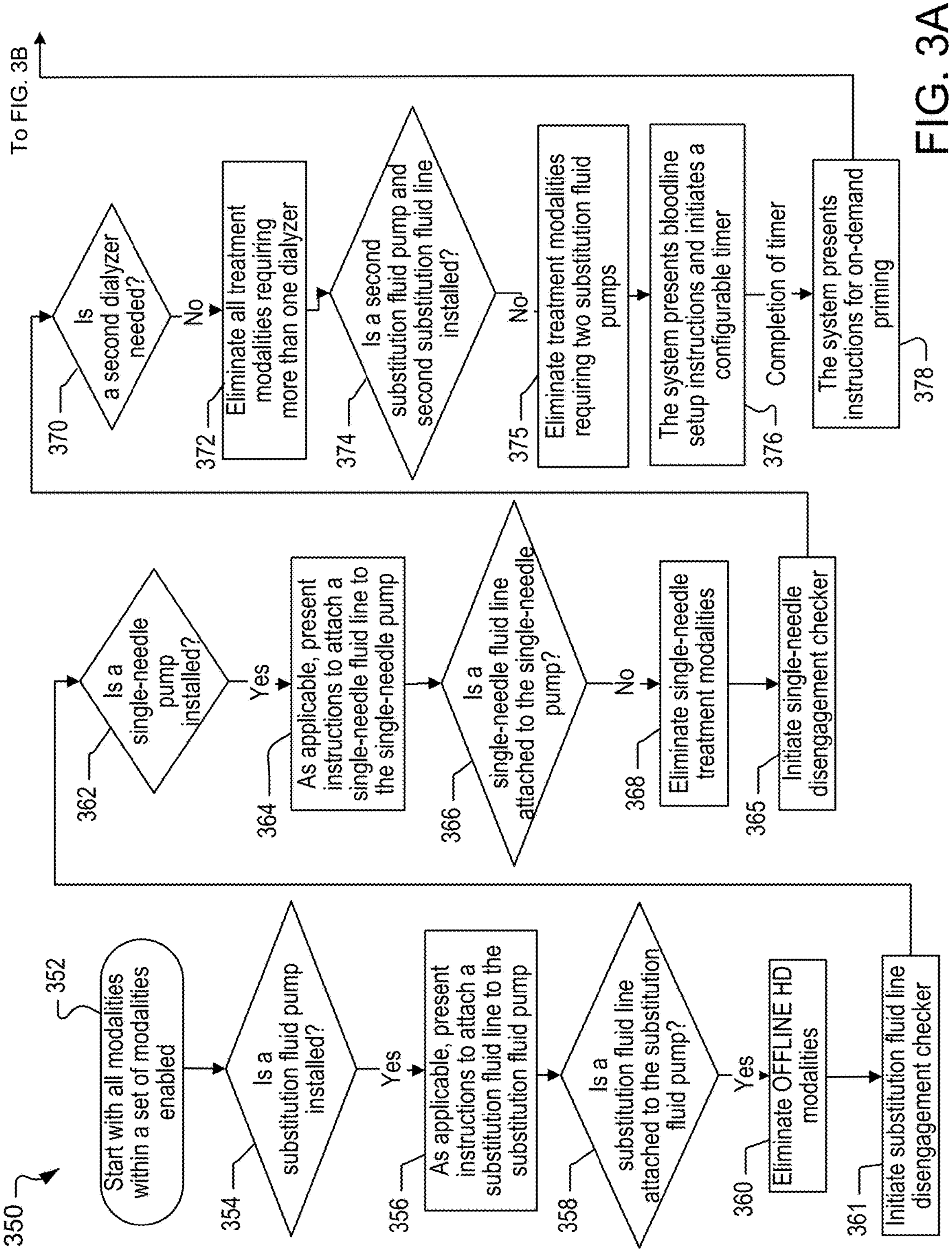
FIGS. 3A and 3B show an example flow chart of a decision process to eliminate modalities for determining available modalities for the blood treatment machine of FIG. 1.
Figure 3B:
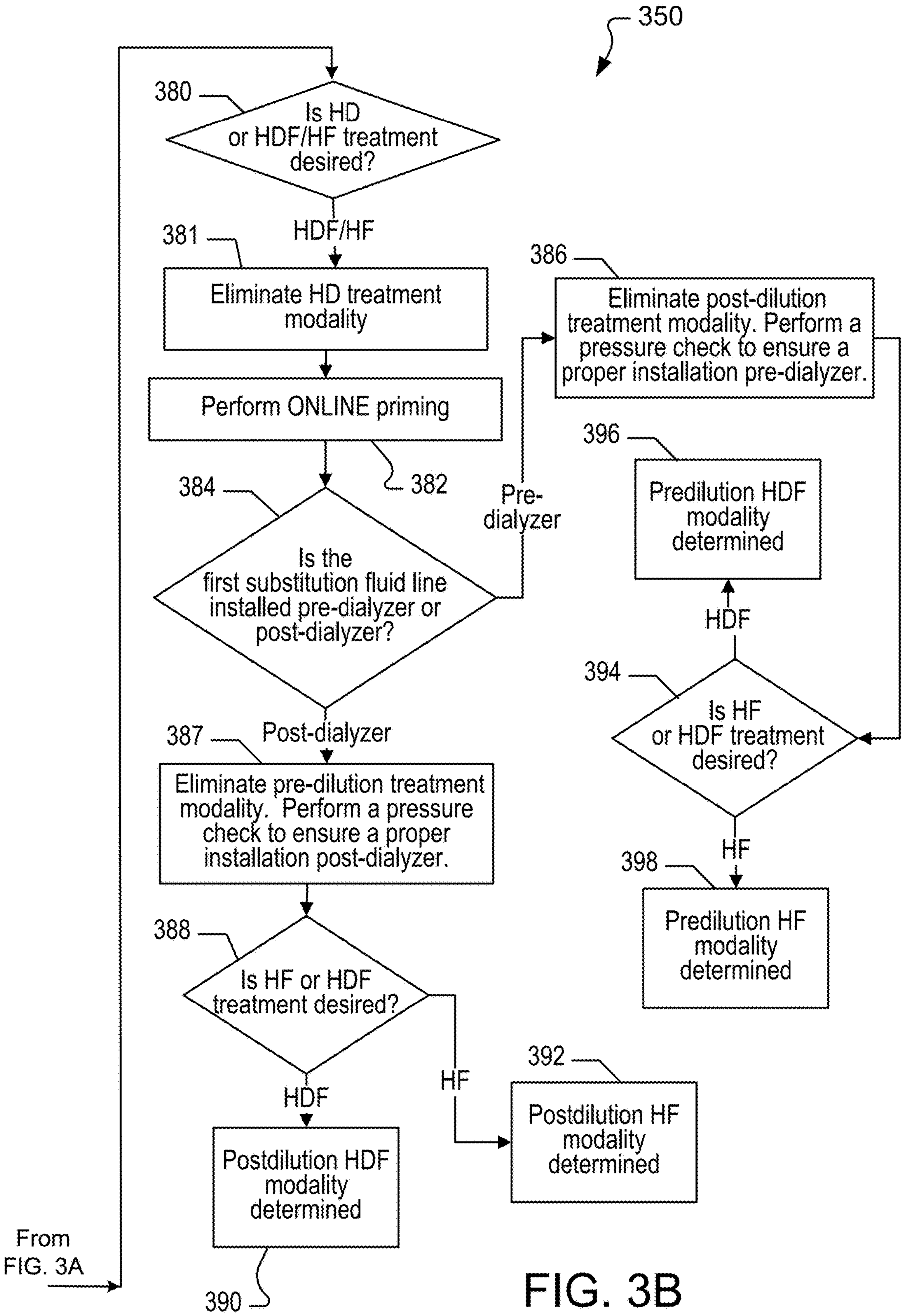

FIGS. 3A and 3B show a flow chart of the disclosed start-up procedure 350 that would occur for the blood treatment machine 100 as shown in FIG. 1. The blood treatment machine 100 begins with all potential treatment modalities within a set of modalities. The "set of modalities" is a predetermined list of modalities that can be performed using the blood treatment machine 100. In this example, the set of modalities includes hemodialysis (HD), hemofiltration (HF), hemodiafiltration (HDF), mixed HDF/HD, mid-dilution, pre-dilution, post-dilution, single-needle, and dual-needle modalities. As the blood treatment machine 100 progress through the flow chart (e.g., via a detection of certain components of the blood treatment machine 100 (e.g., pumps, etc.), a detection of fluid lines attached the blood treatment machine 100 (e.g., substitution fluid lines, single-needle fluid lines, etc.), and/or via user responses to inquiries), the blood treatment machine 100 eliminates treatment modalities that do not apply. This process is further explained below in the context of several examples.

In the example flowchart of FIGS. 3A and 3B, the blood treatment machine 100 begins with all potential treatment modalities within a set of modalities enabled (step 352). The blood treatment machine 100 progressively eliminates modalities from the set of modalities to determine a modality to be used based on whether a particular component (e.g., a substituate pump 206, a single-needle pump 208, etc.) is connected to the blood treatment machine 100 (e.g., as detected via the sensors described above) and based on actions taken by the user during setup.

In this example, information about the presence of the component is first sensed by the sensor and received by the processor of the blood treatment machine 100. The blood treatment machine 100 determines whether a substitution fluid pump (e.g. substitution fluid pump 206), is installed on the blood treatment machine 100 (step 354). If a substitution fluid pump is installed, the blood treatment machine 100 presents instructions the user via user interface 130 to install, as applicable, a substitution fluid line (e.g., substitution fluid line 180) to the substitution fluid pump (step 356).

Blood treatment machine 100 then monitors user interface 130 for operator input and monitors sensor 242 for indication of installation of substitution fluid line 180 into the substitution pump 206. For example, sensor 242 associated with the substitution fluid pump 206 can be used to detect whether a pump line segment of the disposable set is connected to the substituate pump and can transmit that information to the processor of the blood treatment machine

100. In this example, blood treatment machine 100 detects a substitution fluid pump is installed, and resultantly the user is prompted to install substitution fluid line 180 as needed. Sensor 242 then detects substitution fluid line 180 is attached to the substitution fluid pump 206 (step 358). If the blood treatment machine 100 determines that the substitution fluid line 180 is attached to the substitution fluid pump 206, the blood treatment machine 100 eliminates OFFLINE HD modalities but does not eliminate any filtration modalities from the set of modalities in step 360. At this point, the processor would also initiate a disengagement checker where sensor 242 is monitored to ensure the substitution fluid line 180 is not removed (step 361). If removal occurs, the operator would be returned to decision step 356 and a prompt shown in FIG. 5 would be again displayed to allow the operator to either reinstall the substitution fluid (if for example the previous line was leaking), or to confirm that the installation of the substitution fluid line was done in error and an OFFLINE HD treatment was desired.

The blood treatment machine 100 then determines whether a single-needle pump is installed in the extracorporeal blood module (step 362). If a single-needle pump is installed, the blood treatment machine 100 determines if a single-needle treatment modality is desired through display of a message box on user interface 130 instructing the operator to install a single-needle fluid line 190 into the single-needle pump 208 as needed (step 364). As shown in FIGS. 1 and 2A, the blood treatment machine 100 includes a single-needle blood pump 208, and accordingly in step 354 the user would be prompted on user interface 130 to install a single-needle fluid line 190 if a single-needle treatment modality was desired. For example, sensor 244 associated with the single-needle pump 208 can be used to detect whether a single-needle blood fluid line 190 is connected to the single-needle pump 208 and can transmit that information to the processor of the blood treatment machine 100 (step 366). For example, in response to detecting that a single-needle blood pump fluid line 190 is not connected to the single-needle pump 208, the blood treatment machine 100 eliminates all single-needle treatment modalities from the set of modalities (step 368). In this way, only dual-needle modalities would remain. At this point, the processor would also initiate an engagement checker where the sensor associated with the single single-needle pump 208 is monitored for introduction of a single-needle fluid line (step 365). If this occurs, the operator would be returned to decision step 364 to allow the operator to either remove the single-needle fluid line (if for example the arterial blood tubing disposable was incorrectly installed into the single-needle pump), or to confirm that the previous exclusion of a single-needle blood tubing was done in error and was desired for treatment.

The blood treatment machine 100 then determines the necessity for a second dialyzer to be installed (step 370). In a preferred embodiment, step 370 includes a determination as to whether treatment with more than one dialyzer is supported would first be performed electronically by blood treatment machine 100 by detecting the presence or absence of an extra set of fresh and spent dialysate valves, and/or associated pressure transducers necessary to achieve the supply and removal of dialysate to an additional dialyzer using additional dialysate supply and return lines. If the blood treatment machine 100 receives information that the necessary hardware is present to support an additional dialyzer, a message box can then be presented to the user via the user interface 130 to confirm whether the additional dialyzer is intended to be used during blood treatment. Additionally or alternatively, the blood treatment machine 100 presents a prompt, via the user interface 130, asking the user whether a second dialyzer is needed for the blood treatment as part of step 370. In this way, step 370 accounts for the possibility of an additional dialyzer being desired for the blood treatment independent of the presence of hardware to supply dialysate to a second dialyzer.

Generally, an additional dialyzer could supply dialysate passively from a first dialyzer, by using dialysate tubing to connect the outlet of a first dialyzer to the inlet of a second dialyzer, with dialysate supplied by blood treatment machine 100 to the dialysate inlet of a first dialyzer and dialysate then returned to blood treatment machine 100 as it exits the dialysate outlet of a second dialyzer. In this example, the processor receives an indication that blood treatment machine 100 does not include a second set of dialysate lines, and accordingly in step 370 blood treatment machine 100 determines a second dialyzer is not needed. Accordingly, the blood treatment machine 100 eliminates all treatment modalities requiring more than one dialyzer from the set of modalities (step 372). Furthermore, the user interface 130 would not need to present messages regarding the installation of an additional dialyzer; however, in an alternative embodiment thru use of a service mode option, the option could be made available to present instruction for installation of a second dialyzer despite the absence of hardware to supply dialysate to a second dialyzer. In this example, based on the absence of hardware to supply dialysate to a second dialyzer, the subsequent preparation instructions presented on user interface 130 would be reflective of the necessity of needing only a single dialyzer for blood treatment.

The blood treatment machine 100 then receives information regarding whether a second substitution fluid pump is installed on the blood treatment machine and if a second substitution fluid line is attached to the substitution fluid pump (step 374). For example, two substitution fluid pumps are required for mixed HDF/HF treatment modalities using one dialyzer and could be desired for treatments using more than one dialyzer. In this example, blood treatment machine 100 does not include a second substitution fluid pump, and accordingly in step 374 the blood treatment machine 100 would not display a message on user interface 130 regarding the potential installation of a second substitution fluid line and eliminates modalities that require a second substitution fluid pump (e.g., mixed modalities) from the set of modalities (step 375).

The blood treatment machine 100 then presents instructions, via the user interface 130, to the user for installing and priming an extracorporeal blood circuit on the extracorporeal blood module 120 (step 378) reflective of the operator actions taken and hardware detected in decision steps 354, 358, 362, 366, 370, and 374. Generally, as described herein, the extracorporeal blood circuit represents the flow path of the patient's blood through arterial line 170, dialyzer 140, and venous line 195. Additionally, the extracorporeal blood circuit, as described herein, could also include a single-needle fluid line, one or more substitution fluid line, and blood fluid lines connected between the blood outlet of a first dialyzer and the blood inlet of a second dialyzer. The extracorporeal blood module 120 relates to the hardware configuration of the blood treatment machine 100.

Figure 4:
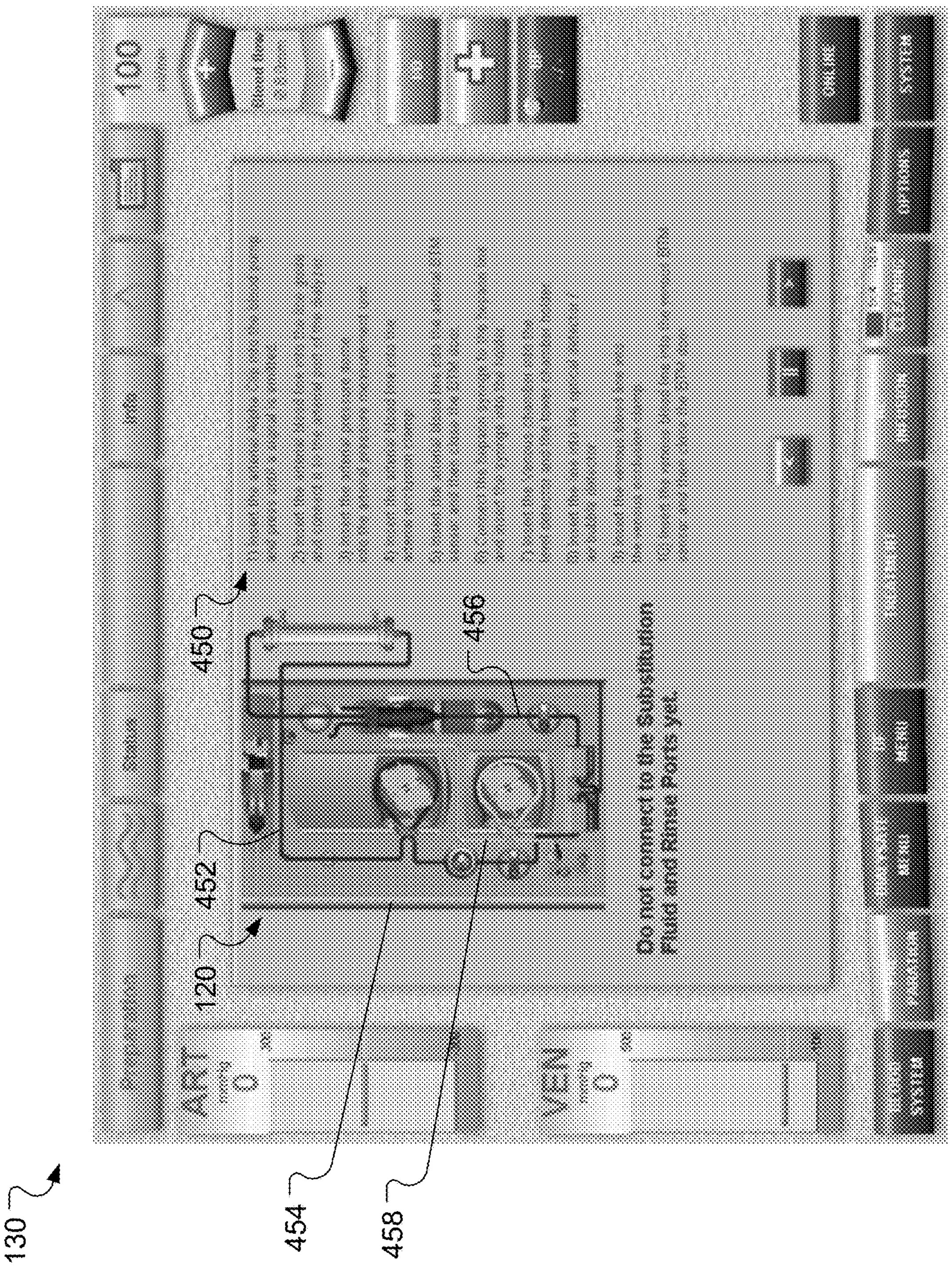
FIG. 4 shows the user interface of the blood treatment machine of FIG. 1 presenting instructions for configuring the blood treatment machine of FIG. 1 in a priming configuration.

FIG. 4 shows the user interface 130 presenting a graphic illustration of the extracorporeal blood module 120 of the blood treatment machine 100 in a priming configuration resultant of the determinations made by blood treatment machine 100 based on associated hardware detection and actions taken by the user articulated in the start-up procedure 350. The extracorporeal blood module 120 is presented on the user interface 130 throughout the setup process to aid the user in configuring the blood treatment machine 100. The user interface 130 can present markers that serve as a visual aid for assisting the user in performing each respective step of the instructions 450 to configure the blood treatment machine 100 in a priming configuration. Referring to FIG. 4, the extracorporeal blood circuit 120 shown on the user interface 130 includes an arterial fluid line 452, a heparin line 454, a substituate line 458, and a venous line 456. Generally, as the user navigates through the prompts and instructions, the extracorporeal blood circuit 120 shown on the user interface 130 is updated by the blood treatment machine 100 to reflect the current configuration of the extracorporeal blood circuit 120 of the blood treatment machine 100.

Figure 5:
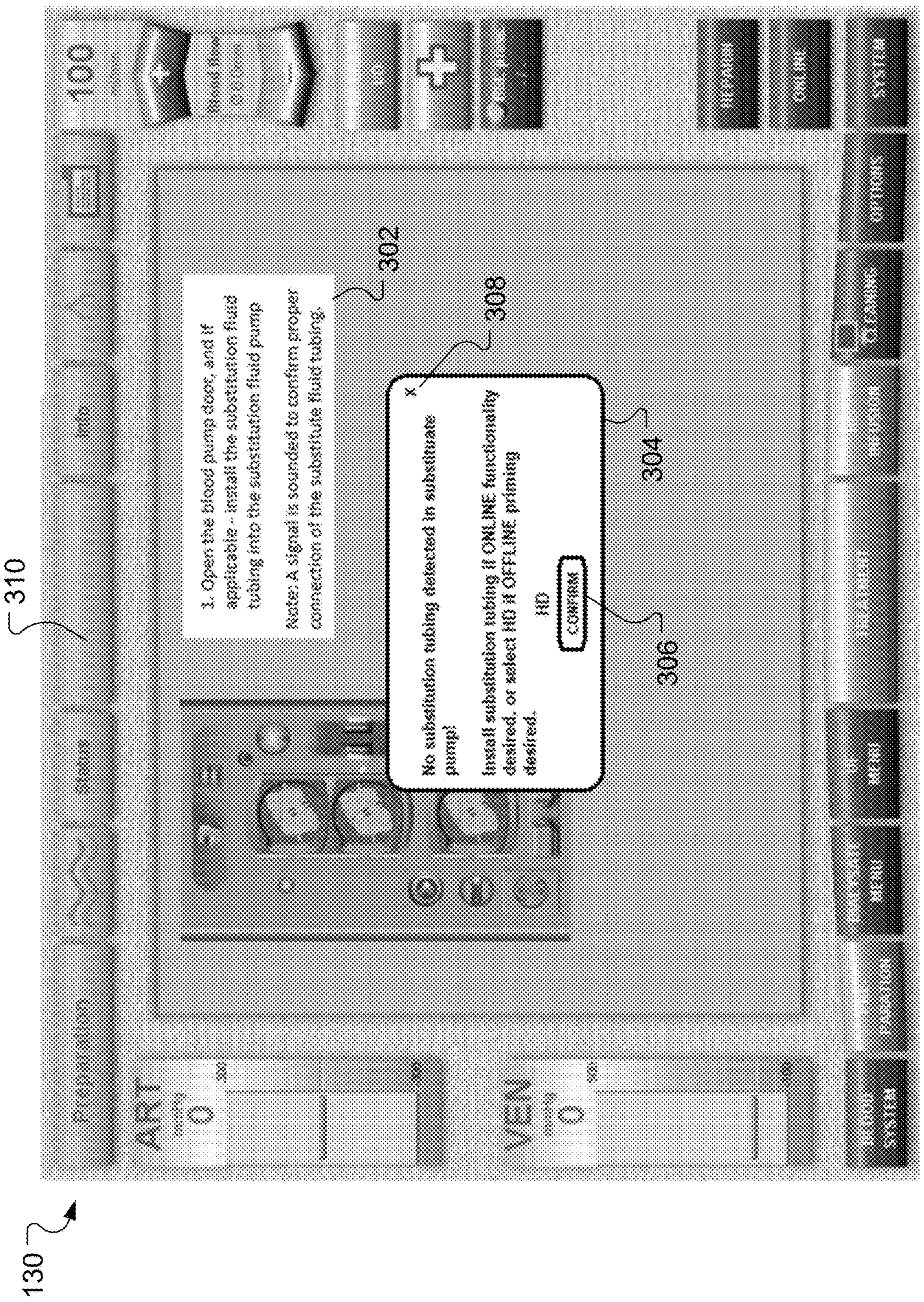
FIG. 5 shows the user interface of the blood treatment machine of FIG. 1 presenting an instruction to install a substitution tubing.

Referring to FIG. 5, when decision step 358 is reached in FIG. 3A, the user interface 130 presents instructions 302 and message box 304 that reads "No substitution tubing detected in substituate pump! Install substitution tubing if ONLINE functionality desired, or select HD if OFFLINE priming desired." The displayed message box 304 also includes a confirmation button 306 that the user can press to indicate that 'HD' OFFLINE priming is desired and that a substitution fluid tubing will not be installed. As noted above, "ONLINE" functionality means that the blood treatment machine 100 produces substituate on-demand via substitution fluid tubing that is required for bloodline preparation, and/or during reinfusion. The blood treatment machine 100 can, for example, produce substituate on demand for use in priming and/or reinfusion for a hemodialysis treatment, and additionally substituate is used for HDF/HF treatment modalities for continuous and bolus administration.

Alternatively, for hemodialysis treatment modalities where the desire is for preparation to be performed with use of saline in-lieu of the substitution fluid lines, "OFFLINE" specific set-up instructions would be subsequently displayed upon selection of the 'HD' button. In this way, the blood treatment machine 100 would not need to display setup instructions for saline-based priming unless specifically confirmed as desired by the user. Message box 304 has an associated X (308) which would allow for minimizing message box 304. The message would be stored in status bar 310, and upon selection of status bar 310 the user interface 130 would again display message box 304.

The processor continuously receives information from the sensor associated with the substituate pump 206 and waits for either the line guide to be installed or the operator to confirm that an OFFLINE hemodialysis treatment is desired before proceeding with the next step in the instructions. In this example, the processor receives an indication that a line guide has been installed into the substituate pump 206 (e.g., indicating that ONLINE priming is desired). In turn, the processor controls the user interface 130 to remove the inquiry 304 automatically and continues presenting instructions and eliminates the OFFLINE HD modality. As progress is made through decision steps 362, 366, 370, and 374 of FIG. 3A, additional message boxes would be presented as deemed necessary by blood treatment machine 100, and then the operator would be instructed to begin setup of the arterial line 170, dialyzer 140, and venous line 195.

In this way, the blood treatment machine 100 performs a first check during start-up to determine whether reusable components such as a first substituate pump, followed by subsequent checks for the presence of: a second substituate pump, additional dialysate lines, and the single-needle pump on the blood treatment machine 100, and additionally if their use is desired. Then, after the initial start-up check is complete, the blood treatment machine 100 performs a second check to determine which disposable components (e.g., the line guides, line sets, etc.) are connected to the blood treatment machine 100.

Figure 6:
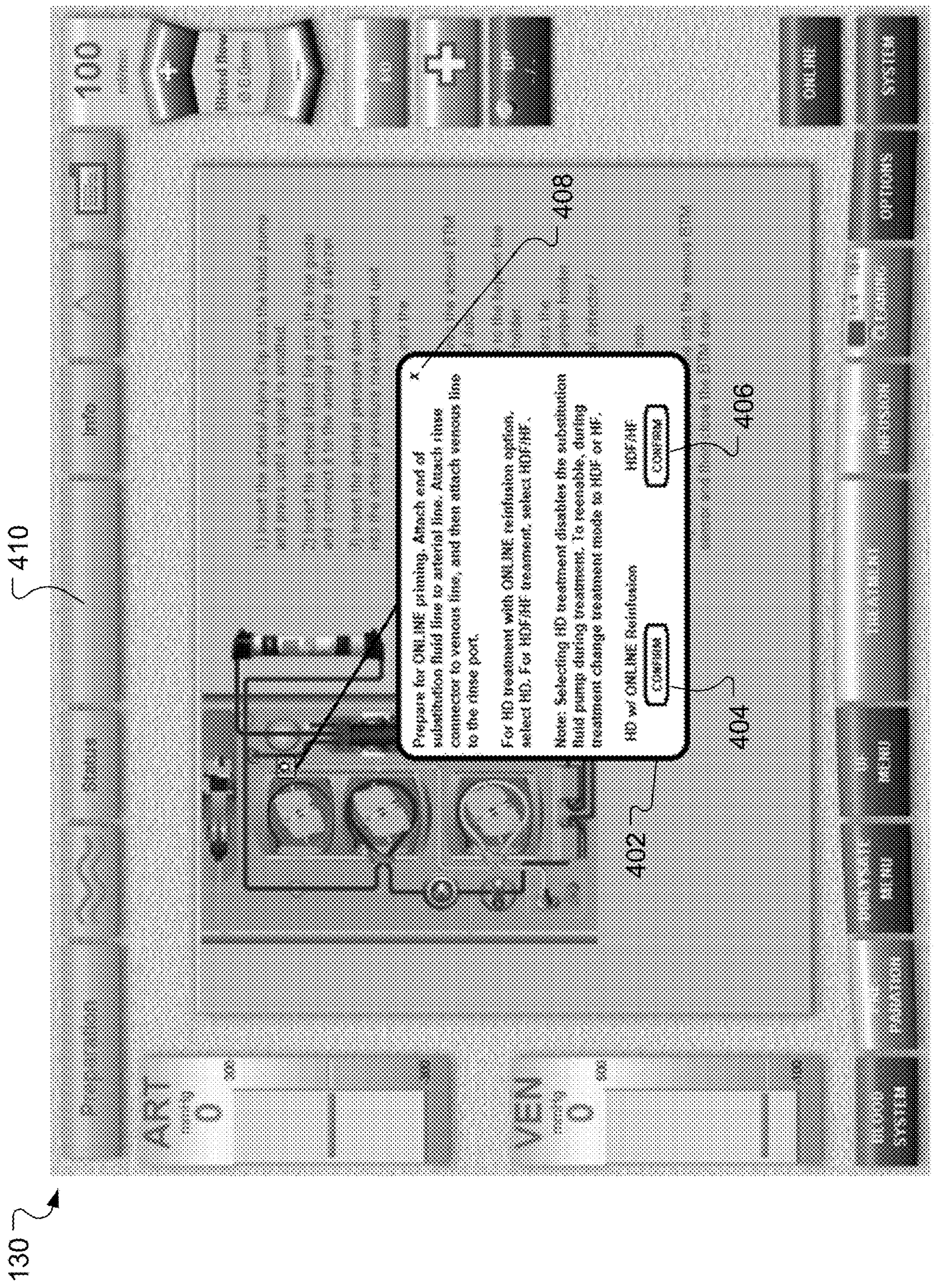
FIG. 6 shows the user interface of the blood treatment machine of FIG. 1 presenting an instruction to assist a user in preparing for on-demand priming using a substitution tubing.

FIG. 6 shows the user interface 130 when decision step 380 is reached in FIG. 3B. User interface 130 presents the extracorporeal blood module 120, as would be expected on blood treatment machine 100, based on the detected machine hardware and the operator actions taken in the preceding decision steps. Additionally, the extracorporeal blood module 120 displays an established arterial line 170, dialyzer 140, and venous line 195 which would have resulted from the operator performing the steps presented in the background of FIG. 6. Upon the presentation of bloodline setup steps in step 376 of FIG. 3, the operator would install arterial bloodline 170 into blood pump 202 which would engage sensor 204. The detection of arterial bloodline 170 would result in the initiation of a configurable timer that would count down as user interface 120 displays additional instructions that would be provided by the operator to install dialyzer 140 and venous bloodline 195. When the configurable timer completes its countdown, which would be meant to provide sufficient time for dialyzer and venous bloodline setup, the user interface 130 presents inquiry message box 402 in front of the bloodline setup instructions (step 380).

Referring back to FIG. 6, message box 402 states, "Prepare for ONLINE priming. Attach end of substitution fluid line to arterial line. Attach rinse connector to venous line, and then attach venous line to rinse port. For HD treatment with ONLINE reinfusion option, select HD. For HDF/HF treatment, select HDF/HF. Note: Selecting HD treatment disables the substitution fluid pump during treatment. To re-enable, during treatment change treatment mode to HDF or HF." The message box 402 includes two options: an HD with ONLINE Reinfusion option (selectable by pressing a first CONFIRM button 404 on the user interface 130) and an HDF/HF option (selectable by pressing a second CONFIRM button 406 on the user interface 130). Message box 402 has an associated X (408) which would allow for minimizing message box 402 if the user still needed to see the background bloodline setup instructions. The message would be stored in status bar 410, and upon selection of status bar 410 the user interface 130 would again display message box 402. In this example, the user presses button 406 to indicate that HDF/HF treatment is desired. Accordingly, the hemodialysis or HD treatment modality would be eliminated from the set of modalities (step 381), and the ONLINE priming would be initiated (step 382).

After completion of ONLINE priming, the operator would then be presented with instructions to attach the arterial and venous lines to the patient (not shown) in preparation for treatment. This mode in between priming and treatment is herein referred to as pre-circulation, where the patient's blood is pulled by the initiation of the blood pump upon patient connection until blood is sensed by the optical detector of blood treatment machine 100. In some embodiments, the venous line would remain connected to rinse port 222 to prevent the introduction of additional fluid into the patient until blood was sensed by the optical detector of blood treatment machine 100. After attachment of the patient as part of the pre-circulation phase of preparation, the user interface 130 presents an instruction to assist a user in preparing the extracorporeal blood circuit for either a pre-dilution or post-dilution treatment. This is part of step 384 of FIG. 3B.

Figure 7:
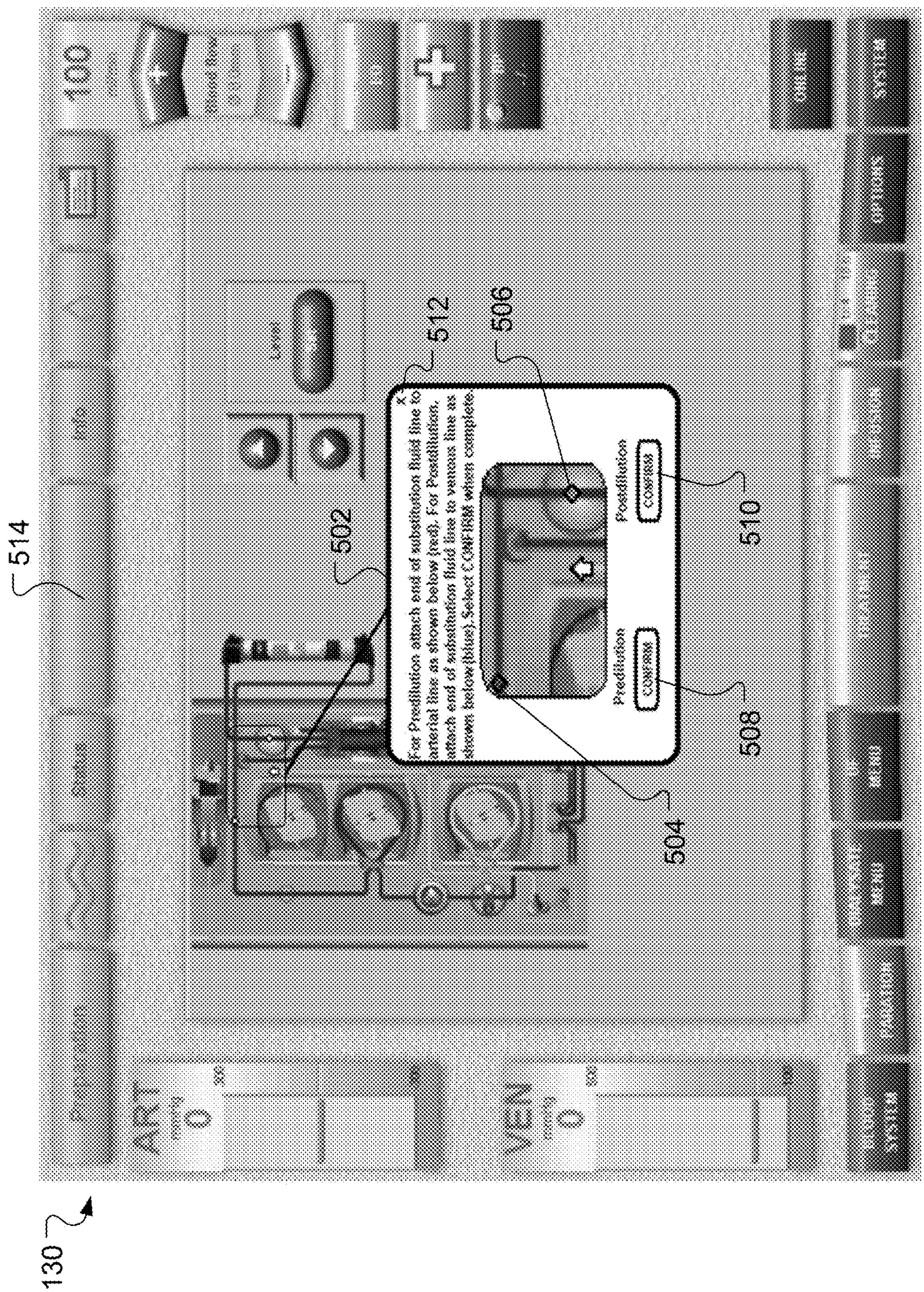
FIG. 7 shows the user interface of the blood treatment machine of FIG. 1 presenting an instruction to assist a user in preparing the blood treatment machine for pre-dilution or post-dilution as part of an on-demand priming configuration.

FIG. 7 shows the user interface 130 when decision step 384 is reached. The user interface 130 presents a message box 502 stating, "For Pre-dilution attach end of substitution fluid line to arterial line as shown below (marker 504). For Post-dilution, attached end of substitution fluid line to venous line as shown below (marker 506). Select CONFIRM when complete." The inquiry 502 includes two options: a Pre-dilution option (selectable by pressing a first CONFIRM button 508 on the user interface 130) and a Post-dilution option (selectable by pressing a second CONFIRM button 510 on the user interface 130). In this example scenario, the user attaches the end of the substitution fluid line to the venous line and presses button 510 to indicate that post-dilution treatment is desired. Accordingly, pre-dilution treatment modalities would be eliminated from the set of modalities, and as described in more detail below, upon confirmation of the selection, the substitution fluid pump will introduce a small fluid bolus to confirm that the substitution fluid line configuration matches the indicated user selection (step 387). At this point only two treatment modalities, dual-needle post-dilution hemodiafiltration (HDF) or dual-needle post-dilution hemodiafiltration (HF) would remain from the set of possible treatment modalities. Message box 502 has an associated X (512) which would allow for minimizing message box 502. The message would be stored in status bar 514, and upon selection of status bar 514 the user interface 130 would again display message box 502.

Figure 8:
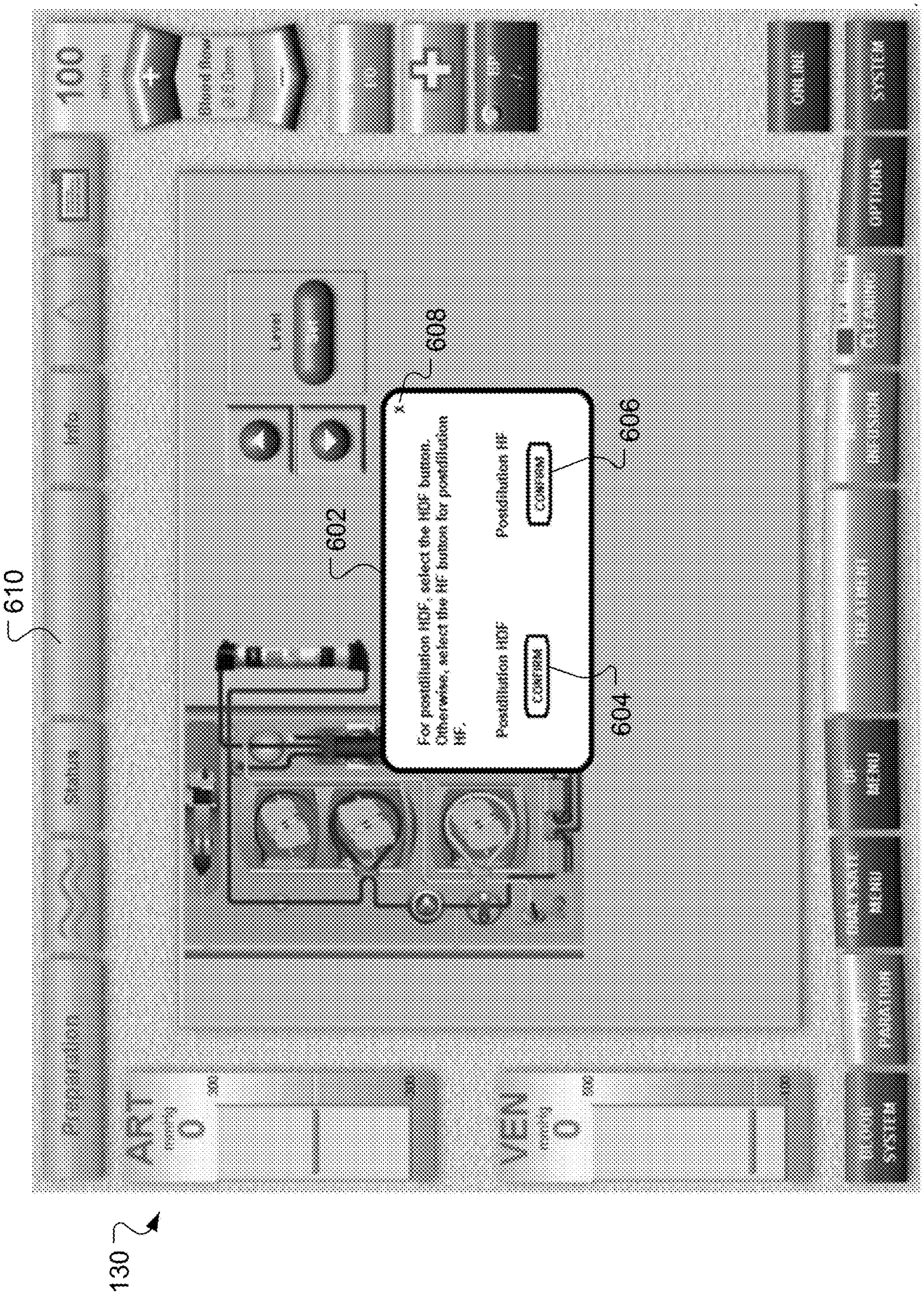
FIG. 8 shows the user interface of the blood treatment machine of FIG. 1 presenting an instruction asking the user to confirm whether a post-dilution hemodiafiltration (HDF) configuration or a post-dilution hemofiltration (HF) configuration is desired.

FIG. 8 shows the user interface 130 when decision step 388 is reached in FIG. 3B. Presenting an instruction asking the user to confirm whether a post-dilution HDF configuration or a post-dilution HF configuration is desired. The user interface 130 presents a message box 602 stating, "For post-dilution HDF, select the HDF button. Otherwise, select the HF button for post-dilution HF." The inquiry 602 includes two options: a Post-dilution HDF option (selectable by pressing a first CONFIRM button 604) and a Post-dilution HF option (selectable by pressing a second CONFIRM button 606). In this example, the user presses button 604 to indicate that a post-dilution HDF treatment is desired. Accordingly, the blood treatment machine 100 makes the final determination that the treatment modality is a dual-needle post-dilution HDF treatment modality (step 390). Message box 602 has an associated X (608) which would allow for minimizing message box 602. The message would be stored in status bar 610, and upon selection of status bar 610 the user interface 130 would again display message box 602.

While certain examples have been described, other examples are possible. For example, if the user indicates that a post-dilution HF treatment is desired, the blood treatment machine 100 would instead make the final decision that the treatment modality is a dual-needle post-dilution HF treatment modality (step 392). In another example, if the user indicates instead that the substitution fluid line will be or is installed before the dialyzer step 384, step 386 would be performed to eliminate post-dilution treatment modalities and to perform a pressure check to ensure appropriate sub stituate line connection, and then a message box analogous to FIG. 8 would then be displayed in decision step 394 to confirm if a pre-dilution HDF or pre-dilution HF treatment modality was desired. Selection of a pre-dilution HF modality would result in the blood treatment machine 100 making the final decision that the treatment modality is a dual-needle pre-dilution HF treatment modality (step 396), while selection of a pre-dilution HF modality would result in the blood treatment machine 100 making the final decision that the treatment modality is a dual-needle pre-dilution HF treatment modality (step 398).

While the blood treatment system 10 discussed above has been described as including a disposable set with a single dialyzer, other arrangements are possible. In some embodiments, for example, the blood treatment system can include a disposable set including two dialyzers arranged in series.

Figure 9A:
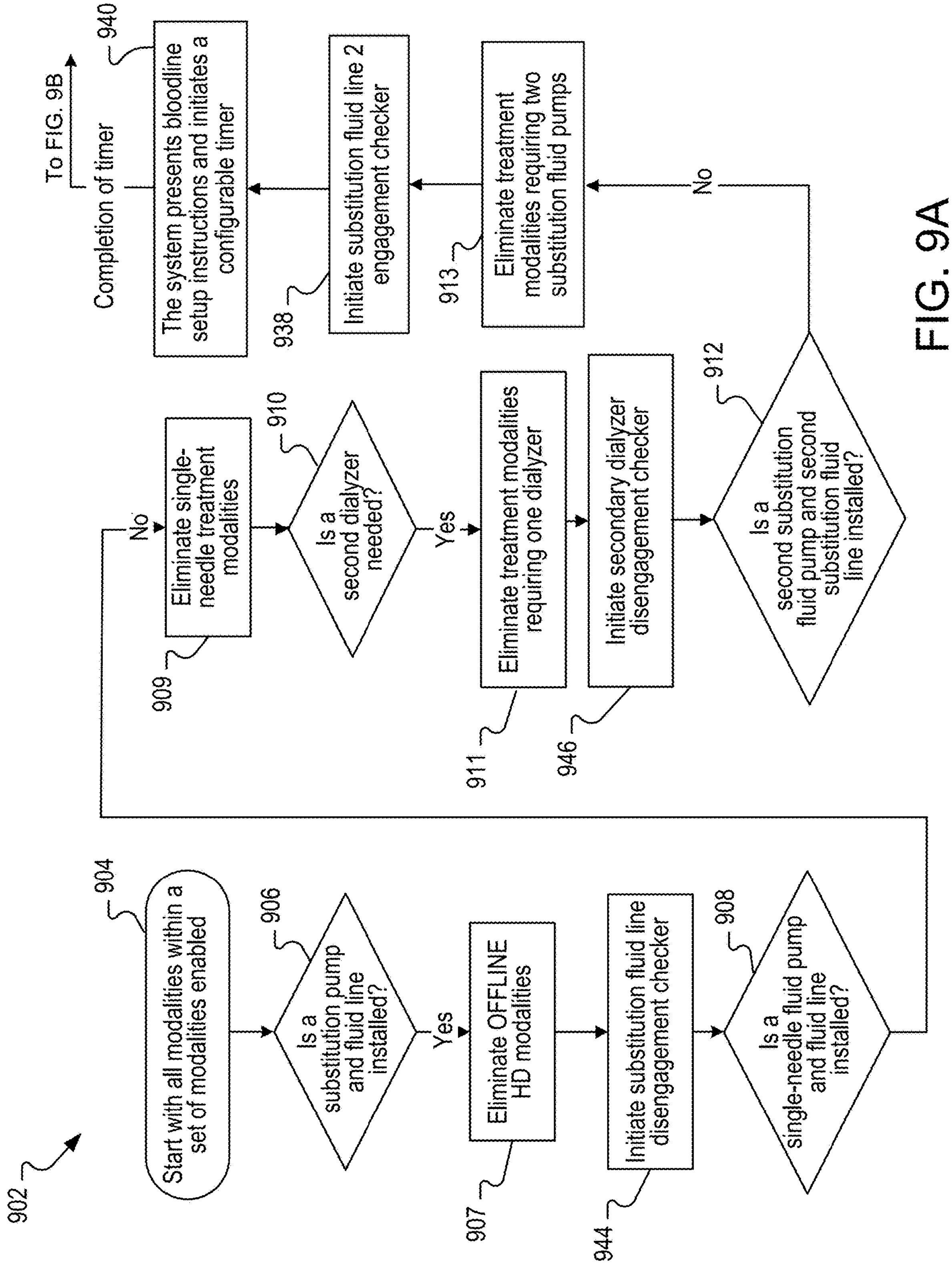
FIGS. 9A and 9B show an example flow chart of a decision process to eliminate modalities for determining available modalities for the blood treatment machine of FIG. 1 when two dialyzers and one substitution fluid line is used.
Figure 9B:
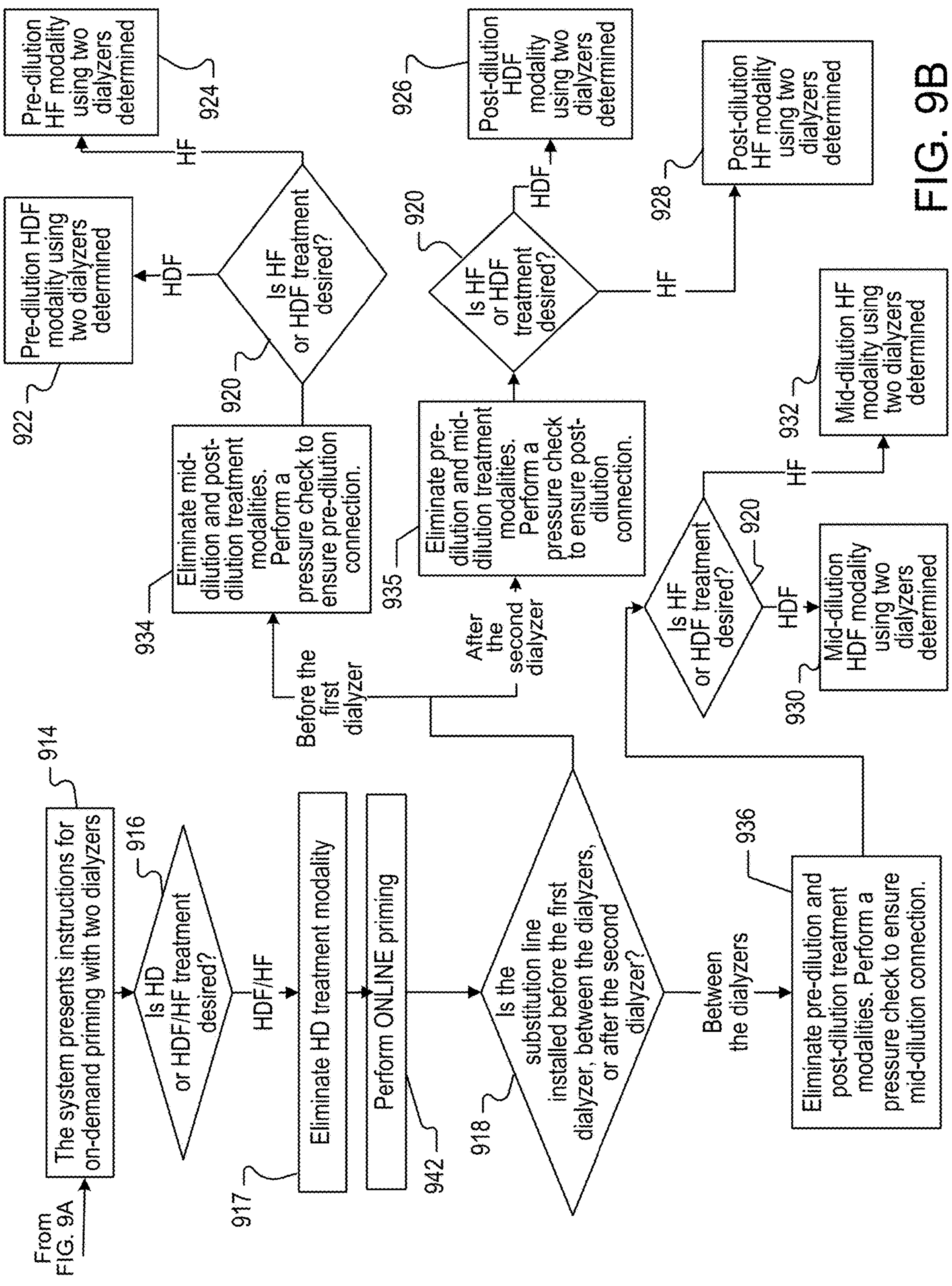

FIGS. 9A and 9B show an example flow chart of a decision process 902 to eliminate treatment modalities for determining available treatment modalities when two dialyzers and one substitution fluid line is used. The flow chart of FIGS. 9A and 9B is similar to the flow chart of FIGS. 3A and 3B except that two dialyzers are used. In this example, the blood treatment machine 100 begins with all potential treatment modalities within a set of modalities (e.g., hemodialysis (HD), hemofiltration (HF), hemodiafiltration (HDF), mixed HDF/HD, mid-dilution, pre-dilution, post-dilution, single-needle, dual-needle, etc.) enabled (step 904).

Information about whether a substitution fluid pump is installed on the blood treatment machine 100 is then received by the blood treatment machine 100 (step 906). In this example, the substitution fluid pump is installed on the blood treatment machine 100 so filtration modalities are not eliminated and the user interface 130 displays a prompt as shown in FIG. 5 instructing the user to install, as applicable, a substitution fluid line to the substitution fluid pump.

Information about whether a substitution fluid line is installed on the substitution fluid pump is also received by the blood treatment machine 100 as part of step 906. For example, a sensor associated with the substituate pump can be used to detect whether a pump line segment of the disposable set is connected to the substituate pump and can transmit that information to the processor of the blood treatment machine 100. Alternatively, a user can indicate that through interaction with a message analogous to that shown in FIG. 5 that an OFFLINE HD treatment modality is desired and that a substitution fluid line is not required for the intended treatment. In an alternative embodiment, a user can indicate that a substitution fluid line is attached to the substituate pump using the user interface 130, if for example the blood treatment machine 100 did not possess a line guide sensor associated with the substitution fluid pump. In this example, the substitution fluid line is attached to the substituate pump so the blood treatment system 100 does not eliminate filtration modalities and eliminates the OFFLINE HD treatment modality (step 907). Upon attachment of the substitution fluid line, the processor would also initiate a disengagement checker (step 944) where sensor 242 is monitored to ensure the substitution fluid line is not removed. If removal occurs, the operator would be returned to decision step 906 and instructions in accordance with FIG. 5 would be again displayed to allow the operator to either reinstall the substitution fluid (if for example the previous line was leaking), or to confirm that the installation of the substitution fluid line was done in error and an OFFLINE HD treatment was desired.

Information about whether a single-needle fluid is installed on the blood treatment machine 100 is then received by the blood treatment machine 100. If a single-needle pump is installed on the blood treatment machine 100, the blood treatment machine 100 determines if a single-needle treatment modality is desired through display of a message box on user interface 130 instructing the operator to install a single-needle blood tubing into the single-needle blood pump as needed (step 908). In this example, the single-needle pump is not installed on the blood treatment machine 100 so the blood treatment system 100 would not display a user prompt on user interface 130 regarding the installation of a single-needle fluid tubing and would eliminate all single-needle treatment modalities from the set of treatment modalities (step 909).

Information about whether a second dialyzer is needed for the desired blood treatment is then received by the blood treatment machine 100 (step 910). In a preferred embodiment, a determination as to whether treatment with more than one dialyzer is supported would first be performed electronically by blood treatment machine 100 by detecting the presence or absence of an extra set of fresh and spent dialysate valves, and/or associated pressure transducers necessary to achieve the supply and removal of dialysate to an additional dialyzer using additional dialysate supply and return lines. When the blood treatment machine receives information that the necessary hardware is present to support an additional dialyzer, a message box can then be presented to the user via the user interface 130 to confirm whether an additional dialyzer is intended to be used during blood treatment. In an alternative embodiment, thru use of a service mode option, the blood treatment machine 100 could be configured to display a message box to the user via the user interface 130 to confirm whether a second dialyzer is needed for the blood treatment in step 910 independent of the detection of hardware for an additional dialyzer being detected by blood treatment machine 100.

In this example, the blood treatment machine 100 detects the necessary hardware to support treatment with a second dialyzer, a message as to the necessity of a second dialyzer is presented to the user on user interface 130, and the user indicates that a second dialyzer is needed for blood treatment using the user interface 130 of the blood treatment machine 100. Accordingly, the blood treatment machine 100 eliminates treatment modalities that require one dialyzer from the set of treatment modalities (step 911) and the subsequent preparation instructions presented on user interface 130 are reflective of the necessity of a second dialyzer. At this point, the processor would also initiate a disengagement checker where the hardware supporting the use of a second dialyzer is monitored to ensure the second set of dialysate lines are not returned to their respective shunt indicative of their removal from the second dialyzer (step 946). If return of the second set of dialysate lines occurs, the operator would be returned to decision step 910 where the operator will affirm that only one dialyzer is desired or alternatively reinstall the dialysate lines to a second dialyzer (if for example a leak in the second dialyzer was observed during priming).

The blood treatment machine 100 then receives information regarding whether a second substitution fluid pump is installed on the blood treatment machine 100 and whether a second substitution fluid line is attached to the second substitution fluid pump (step 912). For example, blood treatment machine 100 can first determine if a second substitution fluid pump is present, and if present a sensor associated with the second substituate pump can be used to detect whether a pump line segment of the disposable set is connected to the substituate pump in the same way as the first substitution fluid pump according to step 906. The sensor can transmit information about the presence of the substitution fluid line to the processor of the blood treatment machine 100. In this example, a second substitution fluid pump is present, a message is displayed on user interface 130 to confirm the necessity of a second substitution fluid pump for the treatment, and a second substitution fluid line is not attached to the second substituate pump and the operator confirms a treatment modality without a second substitution fluid line is desired. Accordingly, the blood treatment system 100 eliminates treatment modalities that require a second substitution fluid line (step 913). For example, mixed HF/HDF treatment modalities are eliminated from the set of modalities. At this point, the processor would also initiate an engagement checker where the sensor associated with the second substitution fluid pump is monitored for introduction of a second substitution fluid line (step 938). If this occurs, the operator would be returned to decision step 912 to allow the operator to either remove the substitution fluid line disposable (if for example the arterial blood tubing disposable was incorrectly installed into the second substitution fluid pump), or to confirm that the previous exclusion of a second substitution fluid line was done in error and the installation of a second substitution fluid line disposable was desired for treatment.

Subsequent presentation of bloodline setup steps would then occur (step 940). The operator would then install arterial bloodline 170 into blood pump 202 which would engage sensor 204. The detection of arterial bloodline 170 would result in the initiation of a configurable timer that would count down as user interface 120 displays additional instructions that would be provided by the operator to install the necessary disposables for the first and second dialyzer.

The blood treatment machine 100 then presents instructions to the user to configure the extracorporeal blood circuit of the blood treatment machine 100 for on-demand priming with two dialyzers (step 914) reflective of the operator actions taken in decision steps 906, 908, 910, and 912. In this way, the instructions include instructions for priming the extracorporeal blood circuit using the substitute fluid line with two dialyzers in a dual-needle configuration.

The blood treatment machine 100 then presents an instruction on the user interface 130 (analogous to FIG. 6) asking the user to confirm whether a HD or HDF/HF treatment modality is desired (step 916). In this example, the user touches a button on the user interface 130 to indicate that an HDF/HF configuration is desired. In turn, the blood treatment machine eliminates the hemodialysis (HD) treatment modality (step 917), and then ONLINE priming of the two dialyzers is performed (step 942).

The blood treatment machine 100 then presents an instruction on the user interface 130 to confirm where the substitution fluid line will be installed (step 918). Response options include before the first dialyzer, between the two dialyzers, and after the second dialyzer. For example, a response of before the first dialyzer indicates to the blood treatment machine 100 that a pre-dilution configuration is desired. Similarly, a response of after the second dialyzer indicates to the blood treatment machine 100 that a post-dilution configuration is desired. Furthermore, a response of between the two dialyzers indicates to the blood treatment machine 100 that a mid-dilution configuration is desired.

Figure 10:
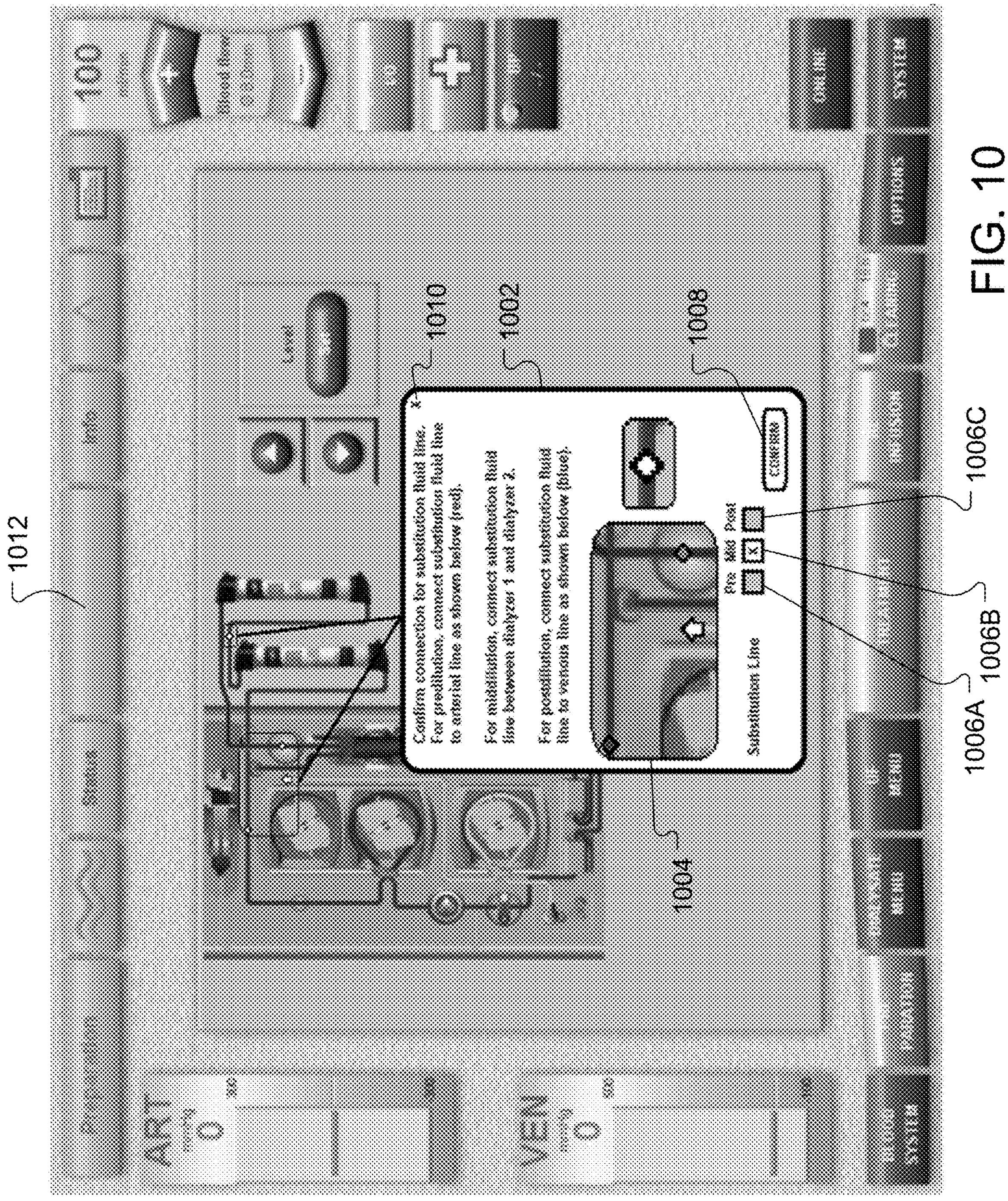
FIG. 10 shows the user interface of the blood treatment machine of FIG. 1 presenting an instruction to assist a user in configuring a blood treatment machine with two dialyzers and one substitution fluid line.

FIG. 10 shows the user interface 130 presenting an instruction 1002 based on the decision step 918 of the flow chart of FIG. 9B. In this example, the instruction 1002 asks the user to "Confirm connection for substitution fluid line. For pre-dilution, connect substitution fluid line to arterial line as shown below (red). For mid-dilution, connect substitution fluid line between dialyzer 1 and dialyzer 2. For post-dilution, connect substitution fluid line to venous line as shown below (blue)." The instruction 1002 includes a graphic illustration 1004 showing the possible substitution fluid line configurations. The user can respond by touching one of three checkboxes 1006A-1006C to indicate pre-dilution, mid-dilution, or post-dilution, respectively. Then the user can touch a button 1008 labeled "CONFIRM" to confirm the selected configuration. In this example, the user indicates that the substitution fluid line is configured for mid-dilution by touching checkbox 1006B. Accordingly, pre-dilution and post-dilution treatment modalities would be eliminated from the set of possible treatment modalities. Additionally, as described in more detail below, upon confirmation of the selection, the substitution fluid pump will introduce a small fluid bolus to confirm that the substitution fluid line configuration matches the indicated user selection (step 936). Message box 1002 has an associated X (1010) which would allow for minimizing message box 1002. The message would be stored in status bar 1012, and upon selection of status bar 1012 the user interface 130 would again display message box 1002.

Referring back to FIG. 10, once the user confirms the selected substitution fluid line configuration, treatment modalities are eliminated and an associated pressure check is performed (steps 934 for placement before the first dialyzer, step 935 for placement after the second dialyzer, and step 936 for placement between the first and second dialyzer) to ensure correct placement of the substituate line, and then the blood treatment machine 100 presents an instruction on the user interface 130 (analogous to FIG. 8) asking the user whether HF or HDF treatment is desired (steps 920). Once the user makes a selection, the blood treatment machine 100 determines the modality. For example, if the user indicates that the substitution fluid line will be or is installed before the first dialyzer in step 918 and the user then indicates that an HDF treatment is desired in step 920, the blood treatment machine 100 determines the modality as a pre-dilution HDF modality with two dialyzers in a dual-needle configuration (step 922). If the user indicates that the substitution fluid line will be or is installed before the first dialyzer in step 918 and the user indicates that an HF treatment is desired in step 920, the blood treatment machine 100 determines the modality as a pre-dilution HF modality with two dialyzers in a dual-needle configuration (step 924).

Similarly, if the user indicates that the substitution fluid line will be or is installed after the second dialyzer in step 918 and the user indicates that an HDF treatment is desired in step 920, the blood treatment machine 100 determines the modality as a post-dilution HDF modality with two dialyzers in a dual-needle configuration (step 926). If the user indicates that the substitution fluid line will be or is installed after the second dialyzer in step 918 and the user indicates that an HF treatment is desired in step 920, the blood treatment machine 100 determines the modality as a post-dilution HF modality with two dialyzers in a dual-needle configuration (step 928).

Furthermore, if the user indicates that the substitution fluid line will be or is installed between the two dialyzers in step 918 and the user indicates that an HDF treatment is desired in step 920, the blood treatment machine 100 determines the modality as a mid-dilution HDF modality with two dialyzers in a dual-needle configuration (step 930). If the user indicates that the substitution fluid line will be or is installed between the two dialyzers in step 918 and the user indicates that an HF treatment is desired in step 920, the blood treatment machine 100 determines the modality as a mid-dilution HF modality with two dialyzers in a dual-needle configuration (step 932).

Figure 11A:
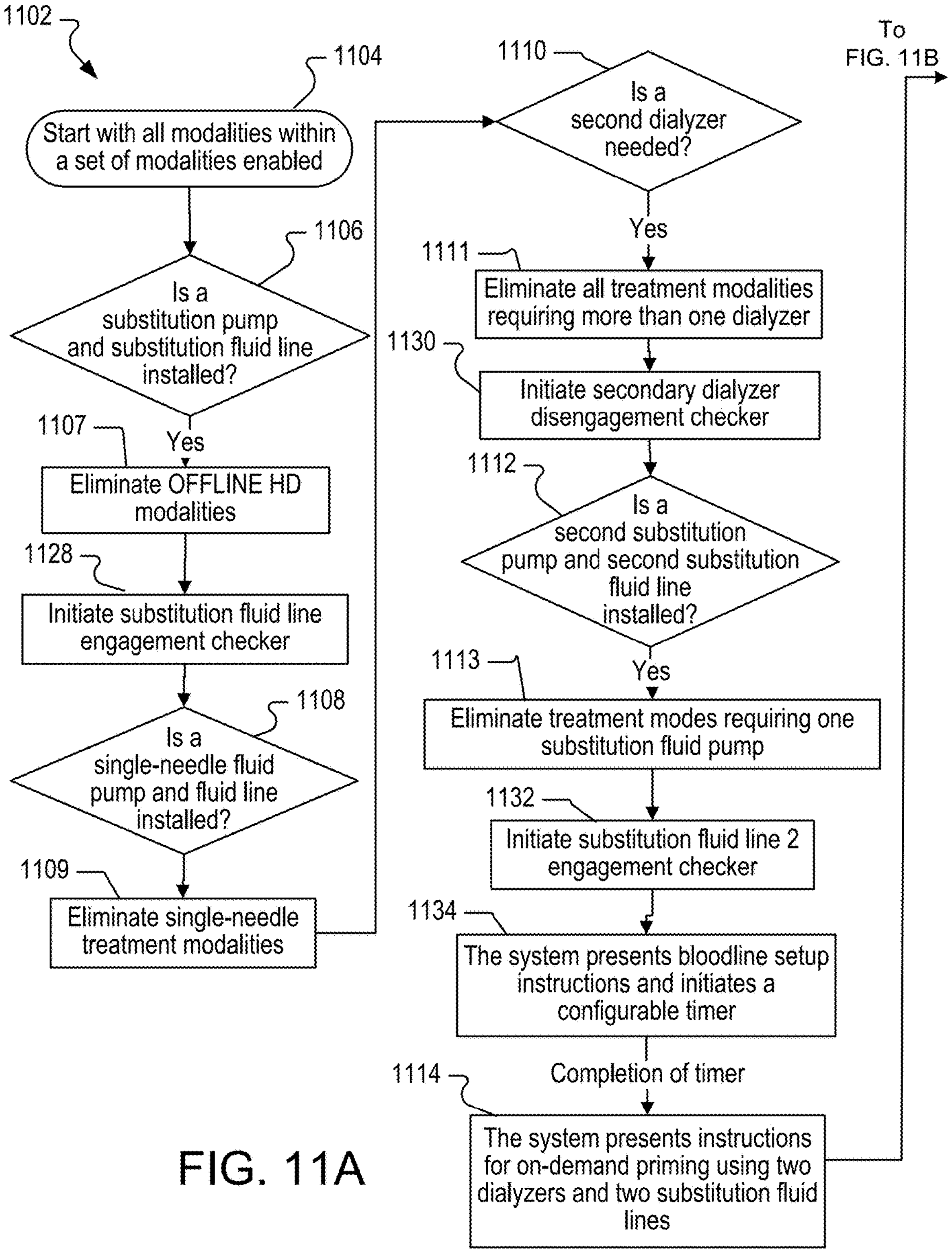
FIGS. 11A and 11B show an example flow chart of a decision process to eliminate modalities for determining available modalities for the blood treatment machine of FIG. 1 when two dialyzers and two substitution fluid lines are used.
Figure 11B:
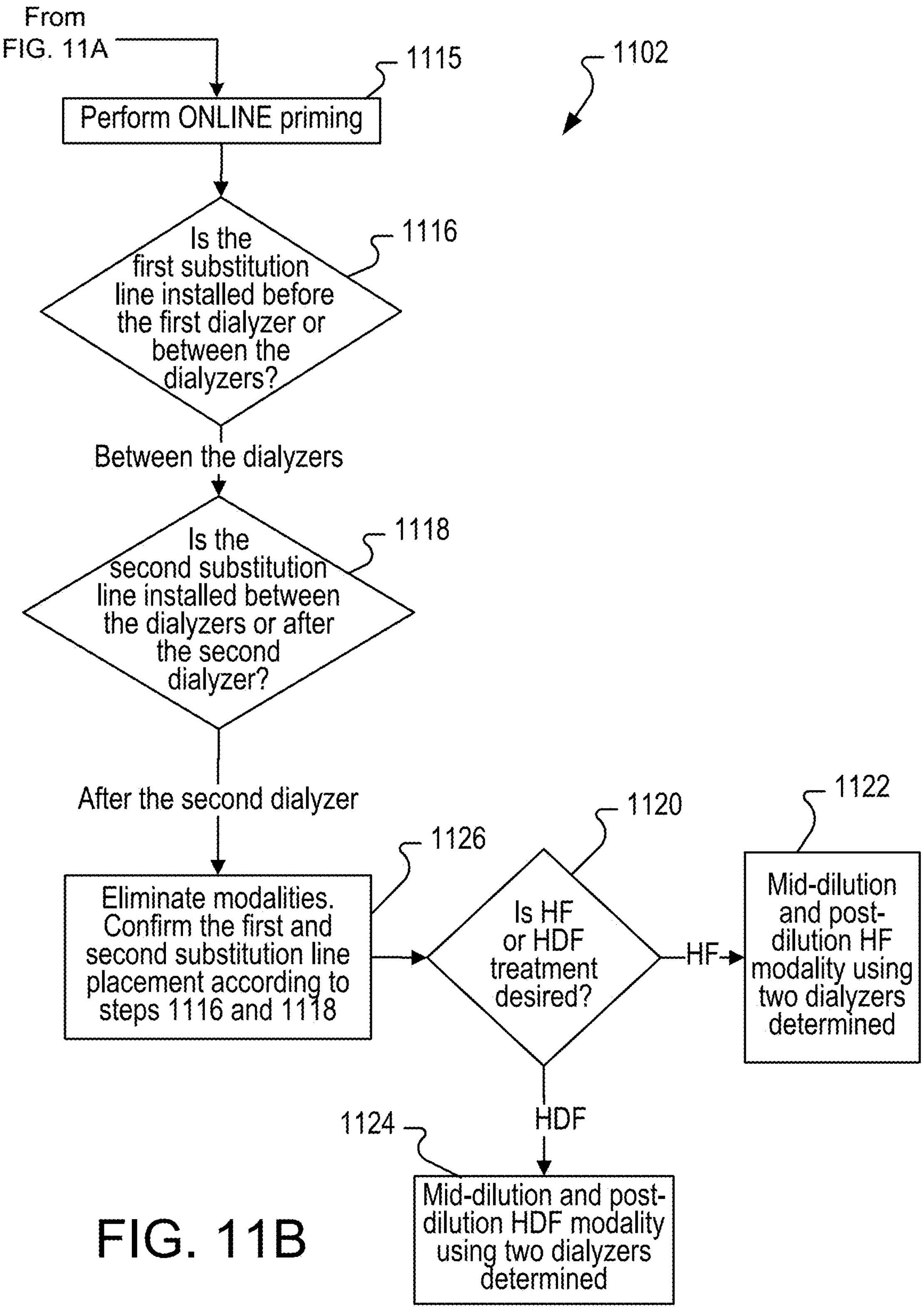

FIGS. 11A and 11B show an example flow chart of a decision process 1102 to eliminate treatment modalities for determining available treatment modalities when two dialyzers and two substitution fluid lines are used. The flow chart of FIGS. 11A and 11B is substantially similar to the flow chart of FIGS. 9A and 9B except that two substitution fluid lines are used. In this example, the blood treatment machine begins with all potential treatment modalities within a set of modalities enabled (step 1104) and receives information regarding whether a substitution fluid pump is installed on the blood treatment machine and whether a substitution fluid line is attached to the substitution fluid pump (step 1106). In this example, a substitution fluid pump is installed on a blood treatment machine, a user interface generates a display as shown in FIG. 4, and the user attaches a substitution fluid line to the substitution fluid pump. Accordingly, the blood treatment machine does not eliminate substitution fluid modalities and eliminates the OFFLINE HD treatment modality (step 1107). At this point, the processor would also initiate a disengagement checker (step 1128) where a sensor is monitored to ensure the substitution fluid line is not removed. If removal occurs, the operator would be returned to decision step 1106 and the message box 304 of FIG. 5 would be again displayed to allow the operator to either reinstall the substitution fluid (if for example the previous line was leaking), or to confirm that the installation of the substitution fluid line was done in error and an OFFLINE HD treatment was desired.

The blood treatment machine receives information regarding whether a single-needle pump is installed on the blood treatment machine. If a single-needle pump is installed on the blood treatment machine, the blood treatment machine determines if a single-needle treatment modality is desired through display of a message box on the user interface instructing the operator to install a single-needle blood tubing disposable into the single-needle blood pump as needed (step 1108). In this example, a single-needle blood pump is not installed so the blood treatment machine does not display a message box on the user interface regarding the installation of a single-needle blood tubing disposable and would eliminates all single-needle treatment modalities from the set of treatment modalities (step 1109).

Then the blood treatment machine receives information regarding whether a second dialyzer is needed for the desired blood treatment modality (step 1110). In this example, blood treatment machine detects the presence of the necessary hardware to support an additional dialyzer, a resultant message is presented to the user via the user interface to confirm whether the additional dialyzer is intended to be used during blood treatment, and the user confirms the necessity of a second dialyzer to be installed for blood treatment. Accordingly, the blood treatment machine eliminates treatment modalities that require one dialyzer from the set of treatment modalities and the subsequent preparation instructions presented on user interface 130 are reflective of the necessity of a second dialyzer (step 1111). At this point, the processor would also initiate a disengagement checker where the hardware supporting the use of a second dialyzer is monitored to ensure the second set of dialysate lines are not returned to their respective shunt indicative of their removal from the second dialyzer (step 1130). If return of the second set of dialysate lines occurs, the operator would be returned to decision step 1110 where the operator will affirm that only one dialyzer is desired or alternatively reinstall the dialysate lines to a second dialyzer (if for example a leak in the second dialyzer was observed during priming).

Then the blood treatment machine receives information regarding whether a second substitution fluid pump is installed on the blood treatment machine and whether a second substitution fluid line is attached to the second substitution fluid pump (step 1112). In this example, blood treatment machine makes a first determination that a second substitution fluid pump is present, and accordingly a message box is displayed on the user interface to install a second substitution fluid line into the second substitution fluid pump as needed, and the user then installs a second substitution fluid line to the second substitution fluid pump. Accordingly, the blood treatment machine eliminates all single substitution fluid line treatment modalities (step 1113). At this point, the processor would also initiate an engagement checker where the sensor associated with the second substitution fluid pump is monitored for introduction of a second substitution fluid line (step 1132). If this occurs, the operator would be returned to decision step 1112 to allow the operator to either remove the substitution fluid line disposable (if for example the arterial blood tubing disposable was incorrectly installed into the second substitution fluid pump), or to confirm that the previous exclusion of a second substitution fluid line was done in error and the installation of a second substitution fluid line disposable was desired for treatment.

Subsequent presentation of bloodline setup steps would occur (step 1134), the operator would install arterial bloodline 170 into blood pump 202 which would engage sensor 204. The detection of arterial bloodline 170 would result in the initiation of a configurable timer that would count down as user interface 120 displays additional instructions that would be provided by the operator to install the necessary disposables for the first and second dialyzer.

The blood treatment machine then presents instructions for on-demand priming using two dialyzers and two substitution fluid lines (1114) reflective of the operator actions taken in decision steps 1106, 1108, 110, and 1112.

The blood treatment machine will perform ONLINE priming (step 1115), and then presents instructions asking the user to confirm the location of the first substitution fluid line (step 1116) and the location of the second substitution fluid line (step 1118).

Figure 12:
FIG. 12 show the user interface of the blood treatment machine of FIG. 1 presenting an instruction to assist a user in configuring a blood treatment machine with two dialyzers and two substitution fluid lines.

FIG. 12 shows a user interface presenting an instruction 1202 based on the decision steps 1116 and 1118 of the flow chart of FIG. 11B. In this example, the instruction 1202 asks the user to "Confirm connections for substitution fluid lines 1 and 2. Connect substitution fluid line 1 to either A) arterial line as shown below (red) or B) between dialyzer 1 and 2. If A), connect substitution fluid line 2 to either between dialyzer 1 and 2 or venous line as shown below (blue). If B), connect substitution fluid line 2 to venous line as shown below (blue)." The instruction 1202 includes a graphic illustration 1204 showing the possible substitution fluid line configurations. The user can respond by touching one of two checkboxes 1206*a*-1206*b* to indicate a pre-dilution or mid-dilution, respectively, for the first substitution fluid line and by touching one of two checkboxes 1208*a*-1208*b* to indicate a mid-dilution or post-dilution, respectively, for the second substitution fluid line. Then the user can touch a button 1210 labeled "CONFIRM" to confirm the selected configuration. In this example, the user indicates that the first substitution fluid line is configured for mid-dilution by touching checkbox 1206B. Accordingly, the user interface is updated to grey out checkbox 1206A and checkbox 1208A and updates checkbox 1208B to suggest that the second substitution fluid line be configured for post-dilution (as the placement of the first substitution fluid line in a mid-dilution configuration eliminates the ability of the second substitution fluid line to also be placed in a mid-dilution configuration). Alternatively, had the user indicated that the first substitution fluid line is configured for pre-dilution by touching checkbox 1206A, accordingly the user interface would update to grey out checkbox 1206B and the user could select either checkbox 1208A or 1208B to confirm the placement of the second substitution fluid line. In another example, had the user indicated that the second substitution fluid line is configured for mid-dilution by touching checkbox 1208A, accordingly the user interface would update to grey out checkbox 1206B and 1208B and updates checkbox 1206A to suggest that the first substitution fluid line be configured for pre-dilution. In a further example, had the user indicated that the second substitution fluid line is configured for post-dilution by touching checkbox 1208B, accordingly the user interface would update to grey out checkbox 1208A and the user could select either checkbox 1206A or 1206B to confirm placement of the first substitution fluid line. Message box 1202 has an associated X (1212) which would allow for minimizing message box 1202. The message would be stored in status bar 1214, and upon selection of status bar 1214 the user interface would again display message box 1202.

As described in more detail below, upon selection of button 1210 to confirm placement of substitution fluid line 1 and substitution fluid line 2, unfeasible treatment modalities are eliminated and the substitution fluid pumps will introduce a small fluid bolus to confirm that the substitution fluid line configurations matches the indicated user selections (step 1126).

Referring back to FIG. 12, once the user confirms the selected configuration as part of steps 1116 and 1118, the blood treatment machine 100 presents an instruction on the user interface (analogous to FIG. 8) asking the user whether HF or HDF treatment is desired (step 1120). Once the user makes a selection, the blood treatment machine determines the final treatment modality. In this example, if the user indicates that an HF treatment is desired, the blood treatment machine determines the treatment modality as a mid-dilution and post-dilution HF treatment modality using two dialyzers (step 1122). Alternatively, if the user indicates that an HDF treatment is desired, in this example the blood treatment machine determines the modality as a mid-dilution and post-dilution HDF treatment modality using two dialyzers (step 1124).

While certain examples have been described, other examples are possible. For example, depending on the actions of the user in decision steps 1116, 1118, and 1120, all of the following treatment modalities would be possible: a pre-dilution and mid-dilution HDF treatment modality using two dialyzers, a pre-dilution and mid-dilution HF treatment modality using two dialyzers, a pre-dilution and post-dilution HDF treatment modality using two dialyzers, or a pre-dilution and post-dilution HF treatment modality using two dialyzers.

Figure 13A:
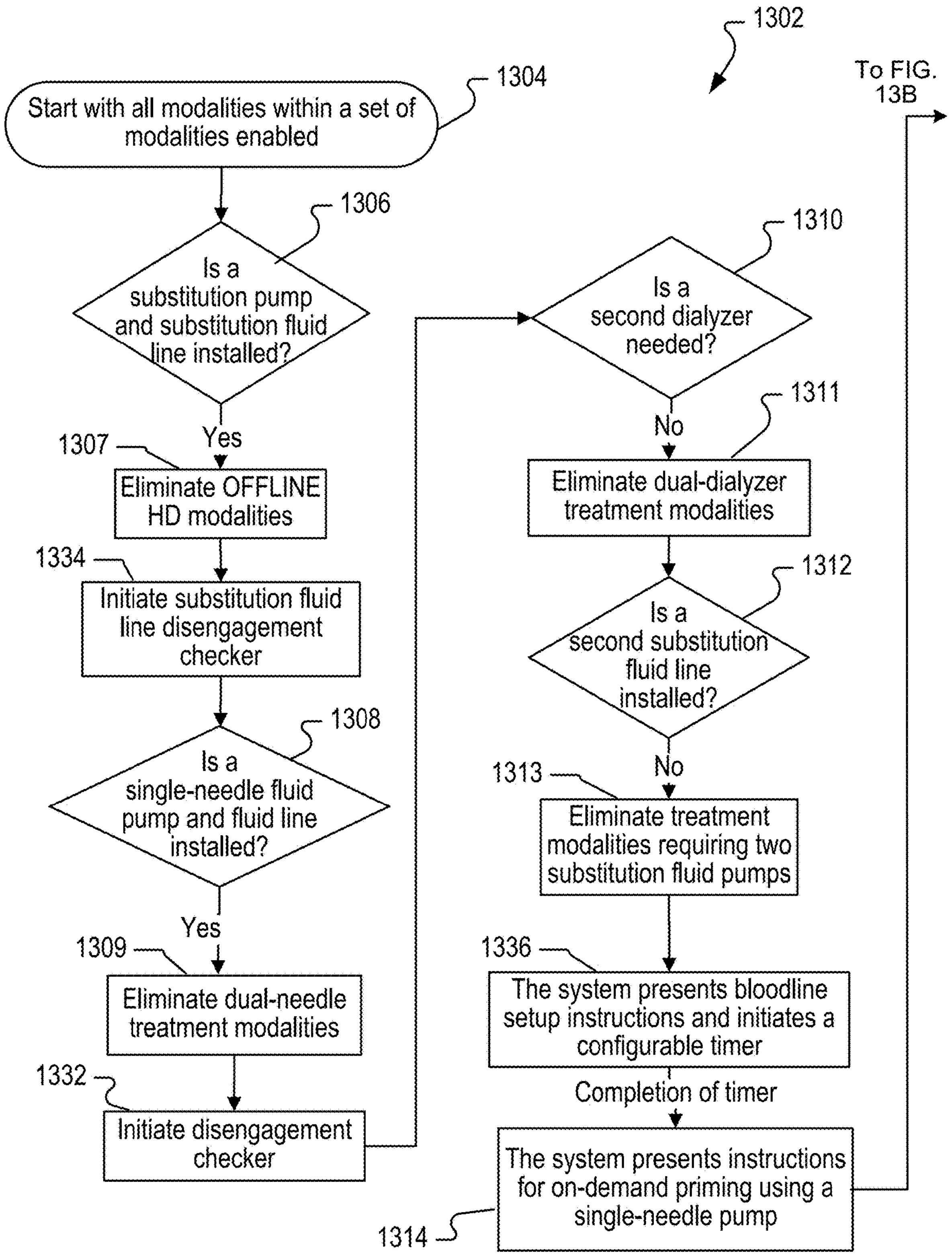
FIGS. 13A and 13B show an example flow chart of a decision process to eliminate modalities for determining available modalities for the blood treatment machine of FIG. 1 when a single-needle pump is used.
Figure 13B:
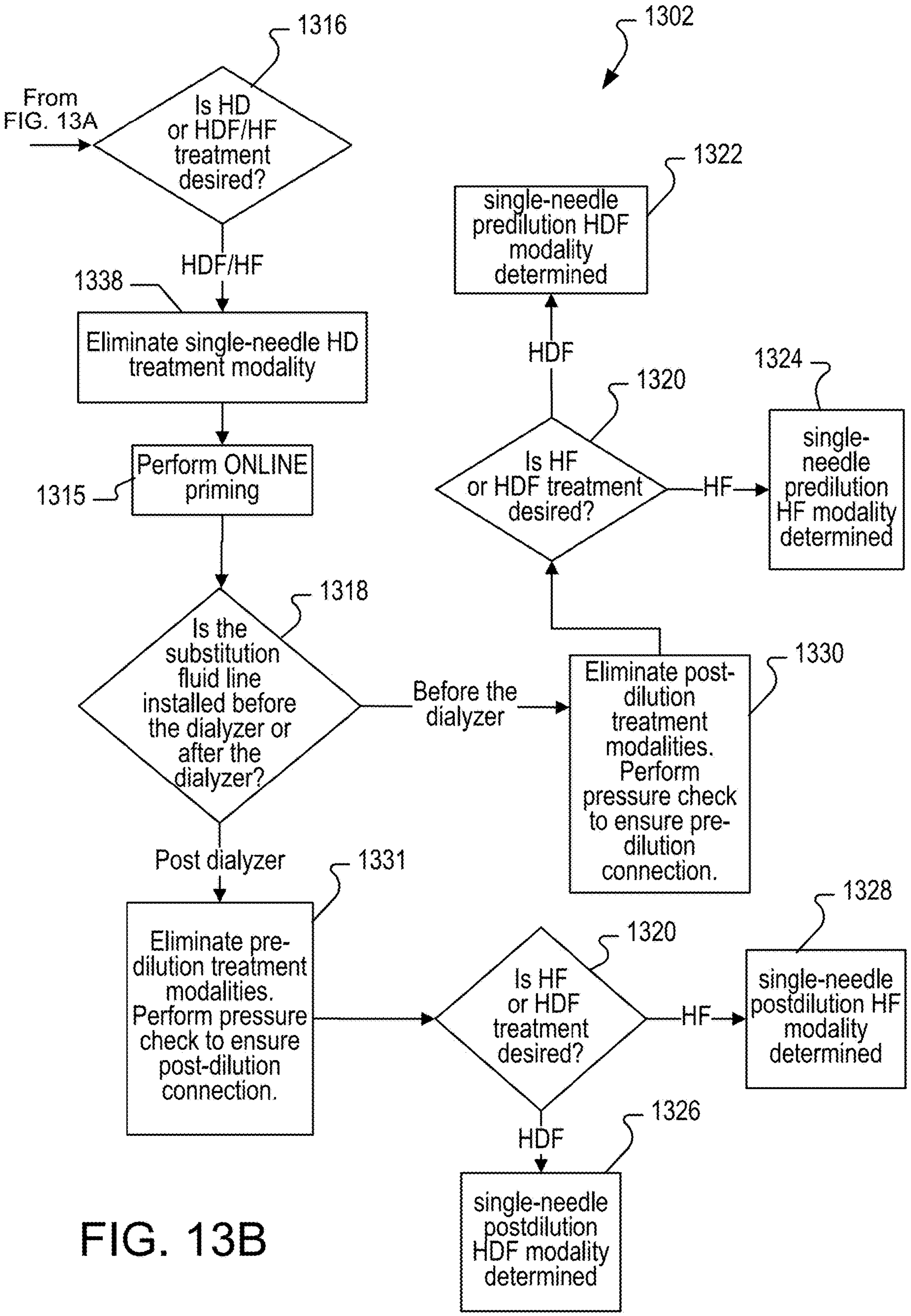

FIGS. 13A and 13B show an example flow chart of a decision process 1302 to eliminate treatment modalities for determining available treatment modalities for the blood treatment machine of FIG. 1 when a single-needle pump is used. The flow chart of FIGS. 13A and 13B is substantially similar to the flow chart of FIGS. 3A and 3B except that a single-needle fluid pump is used. In this example, the blood treatment machine 100 begins with all potential treatment modalities within a set of modalities enabled (step 1304) receives information regarding whether a substitution fluid pump is installed on the blood treatment machine 100 and if installed whether a substitution fluid line is attached to the substitution fluid pump (step 1306). In this example, a substitution fluid pump is installed on blood treatment machine 100 so substitution fluid modalities are not eliminated and the user interface 130 displays FIG. 5 instructing the user to install, as applicable, a substitution fluid line to the substitution fluid pump and this action is taken by the user. Accordingly, the blood treatment machine does not eliminate substitution fluid modalities and eliminates the OFFLINE HD treatment modality (step 1307). At this point, the processor would also initiate a disengagement checker (step 1334) where a sensor is monitored to ensure the substitution fluid line is not removed. If removal occurs, the operator would be returned to decision step 1306 and the message box 304 of FIG. 5 would be again displayed to allow the operator to either reinstall the substitution fluid (if for example the previous line was leaking), or to confirm that the installation of the substitution fluid line was done in error and an OFFLINE HD treatment was desired.

The blood treatment machine 100 receives information regarding whether a single-needle pump is installed. If a single-needle pump is installed on the blood treatment machine 100, the blood treatment machine 100 determines if a single-needle treatment modality is desired through display of a message box on user interface 130 instructing the operator to install a single-needle blood tubing disposable into the single-needle blood pump as needed in an analogous fashion to how the user interface 130 prompts the user to install substitution fluid tubing in FIG. 5 (step 1308). In this example, a single-needle blood tubing disposable is attached to the single-needle pump so the blood treatment machine does not eliminate single-needle treatment modalities and instead eliminates dual-needle treatment (step 1309). Additionally, the user interface 130 updates the preparation screen to reflect the presence of the single-needle blood pump tubing. In some embodiments, the indication of the installation of the single-needle blood tubing is performed strictly through user interaction with the user interface 130 (to account for a blood treatment machine 100 that lacks a sensor to detect the fluid line). At this point, the processor would also initiate a disengagement checker (step 1332) where sensor 244 is monitored for the removal of the single-needle blood tubing. If this occurs, the operator would be returned to decision step 1308 to allow the operator to either reinstall the single-needle blood tubing disposable (if for example it was discovered the single-needle blood tubing disposable had a leak during priming), or to confirm that the previous inclusion of a single-needle blood tubing was done in error and was single-needle treatment was not desired.

Then the blood treatment machine 100 receives information regarding whether a second dialyzer is either installed and/or needed for blood treatment (step 1310). In this example, the processor receives an indication that blood treatment machine 100 does not include a second set of dialysate lines, and accordingly that a second dialyzer is not needed, so the blood treatment machine 100 does not eliminate single dialyzer modalities. Instead, the blood treatment machine 100 eliminates dual dialyzer modalities (step 1311).

Then the blood treatment machine receives information regarding whether a second substitution fluid pump is installed on the blood treatment machine and whether a second substitution fluid line is attached to the second substitution fluid pump (step 1312). In this example, a second substitution fluid pump is not installed, and accordingly eliminates treatment modalities that require a second substitution fluid line (step 1313).

Subsequent presentation of bloodline setup steps would occur (step 1336), the operator would install arterial bloodline 170 into blood pump 202 which would engage sensor 204. The detection of arterial bloodline 170 would result in the initiation of a configurable timer that would count down as user interface 120 displays additional instructions that would be provided by the operator to install the necessary disposables for the single-needle dialysis with one dialyzer.

The blood treatment machine 100 then presents instructions for on-demand priming using a single-needle pump (1314) reflective of the operator actions taken in decision steps 1306, 1308, 1310, and 1312. The blood treatment machine 100 then presents an instruction on the user interface 130 (analogous to FIG. 6) asking the user whether a single-needle HD or HDF/HF treatment modality is desired (step 1316). In this example, the user indicates that a single-needle HDF/HF configuration is desired. In turn, the blood treatment machine 100 eliminates the single-needle hemodialysis (HD) treatment modality (step 1338) and will then perform ONLINE priming (step 1317).

The blood treatment machine 100 then presents instructions asking the user to confirm where the substitution fluid line will be installed in a screen analogous to FIG. 10 (step 1318). The response options include before the dialyzer (pre-dilution) and after the dialyzer (post-dilution). As described in more detail below, upon confirmation of the substitution fluid line, the unfeasible treatment modality based on the substitution fluid line connection will be eliminated and then the substitution fluid pump will introduce a small fluid bolus to confirm that the substitution fluid line configuration matches the indicated user selection (steps 1330 and 1331).

The blood treatment machine 100 then presents an instruction on the user interface 130 asking the user whether an HDF or HF treatment is desired (steps 1320).

Once the user makes a selection to step 1320, the blood treatment machine 100 determines the treatment modality. If the user indicates that the substitution fluid line will be installed or is installed before the dialyzer in step 1318 and that an HDF blood treatment is desired in step 1320, the blood treatment machine 100 determines that the modality is a single-needle pre-dilution HDF modality (step 1322). Similarly, if the user indicates that the substitution fluid line will be installed or is installed before the dialyzer in step 1318 and that an HF blood treatment is desired in step 1320, the blood treatment machine 100 determines that the modality is a single-needle pre-dilution HF modality (step 1324).

Alternatively, if the user indicates that the substitution fluid line will be installed or is installed after the dialyzer in step 1318 and that an HDF blood treatment is desired in step 1320, the blood treatment machine 100 determines that the modality is a single-needle post-dilution HDF modality (step 1326). Similarly, if the user indicates that the substitution fluid line will be installed or is installed after the dialyzer in step 1318 and that an HF blood treatment is desired in step 1320, the blood treatment machine 100 determines that the modality is a single-needle post-dilution HF modality (step 1328).

While certain examples have been described, other examples are possible. For example, depending on the actions of the user in decision steps 1306, 1310, 1312, 1316, 1318, and 1320, all of the following single-needle treatment modalities with the appropriate preparation steps would be possible: hemodialysis (with OFFLINE preparation), hemodialysis (with ONLINE preparation), a pre-dilution HDF treatment modality using two dialyzers, a pre-dilution HF treatment modality using two dialyzers, a mid-dilution HDF treatment modality using two dialyzers, a mid-dilution HF treatment modality using two dialyzers, a post-dilution HDF treatment modality using two dialyzers, a post-dilution HF treatment modality using two dialyzers, a pre-dilution and mid-dilution HDF treatment modality using two dialyzers, a pre-dilution and mid-dilution HF treatment modality using two dialyzers, a pre-dilution and post-dilution HDF treatment modality using two dialyzers, or a pre-dilution and post-dilution HF treatment modality using two dialyzers.

Figure 14:
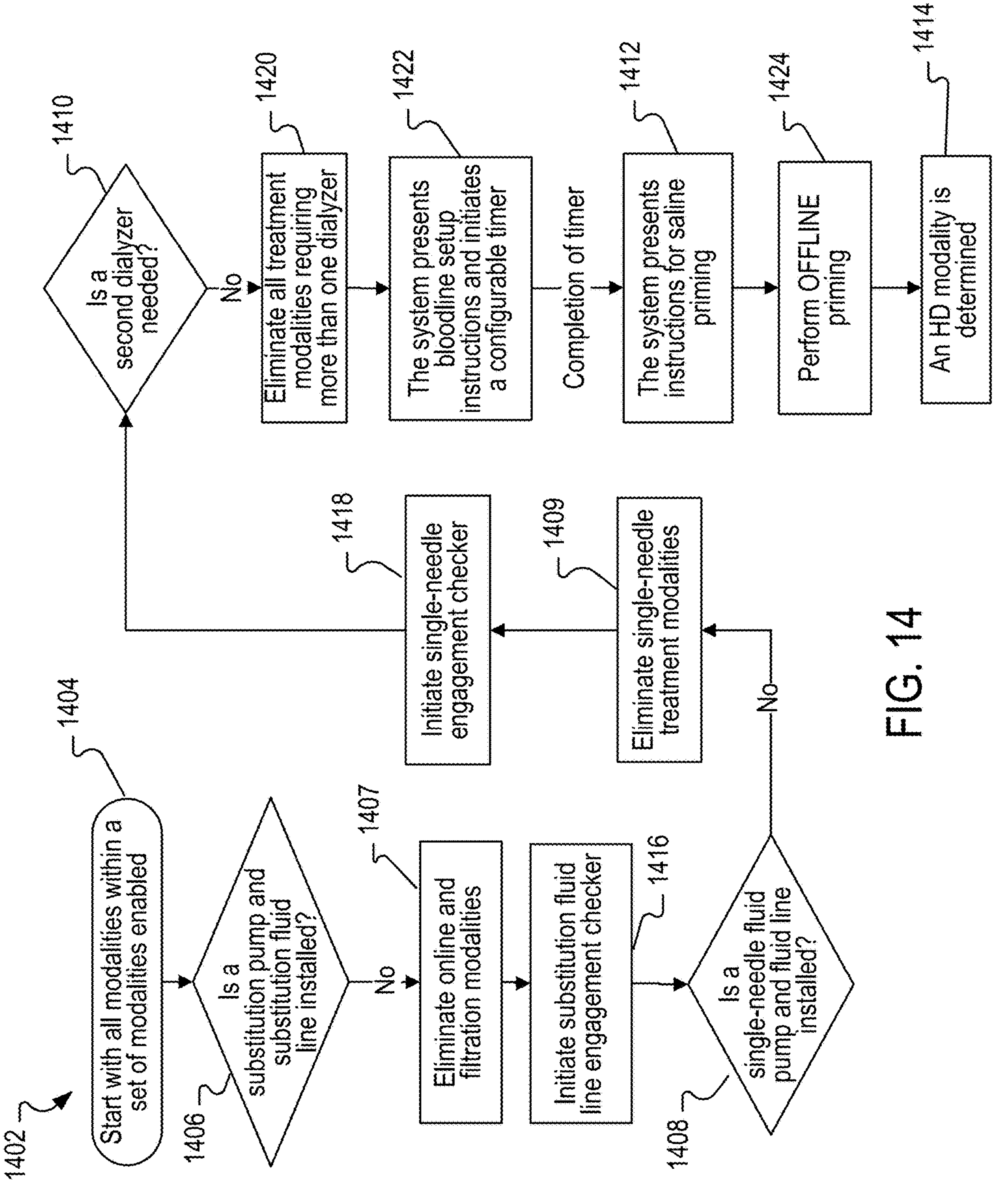
FIG. 14 is an example flow chart of a decision process to eliminate modalities for determining available modalities for the blood treatment machine of FIG. 1 when a substitution fluid lines are not used.

FIG. 14 is an example flow chart of a decision process 1402 to eliminate modalities for determining available modalities for the blood treatment machine of FIG. 1 when substitution fluid lines are not used.

In this example, the blood treatment machine 100 begins with all modalities within a set of modalities enabled (step 1404) receives information regarding whether a substitution fluid pump is installed on the blood treatment machine 100 and whether a substitution fluid line is attached to the substitution fluid pump (step 1406). In this example, a substitution fluid pump is installed on blood treatment machine 100 so substitution fluid modalities are not eliminated and the user interface 130 displays FIG. 4 instructing the user to install, as applicable, a substitution fluid line to the substitution fluid pump. In this example, confirmation button 306 is selected and substitution fluid tubing is not installed. Resultantly, blood treatment machine 100 eliminates all online and filtration modalities from the set of modalities (step 1407). At this point, the processor would also initiate an engagement checker (step 1416) where a sensor (e.g., similar to sensor 204) is monitored for introduction of a substitution fluid line. If introduction of a substitution fluid line occurs, the operator would be returned to decision step 1406 to allow the operator to either remove the substitution fluid line (if for example the arterial fluid line was incorrectly installed into the substitution fluid pump), or to confirm that the previous exclusion of a substitution fluid line was done in error and was desired for treatment.

The blood treatment machine 100 receives information regarding whether a single-needle pump is installed. If a single-needle pump is installed on the blood treatment machine 100, the blood treatment machine 100 determines if a single-needle treatment modality is desired through display of a message box on user interface 130 instructing the operator to install a single-needle blood tubing disposable into the single-needle blood pump as needed (step 1408). In this example, a single-needle blood pump is installed, but the operator does not install single-needle blood pump tubing when prompted and confirms the desire for a dual-needle treatment resulting in single-needle treatment modalities being eliminated (step 1409). At this point, a single-needle engagement checker would be initiated (step 1418). If introduction of a single-needle fluid line occurs, the operator would be returned to decision step 1408 to allow the operator to either remove the single-needle fluid line (if for example the arterial fluid line was incorrectly installed into the single-needle fluid pump), or to confirm that the previous exclusion of a single-needle fluid line was done in error and was desired for treatment.

Then the blood treatment machine 100 receives information regarding whether a second dialyzer is either installed and/or needed for blood treatment (step 1410). In this example, the necessary hardware for a second dialyzer is not installed so the blood treatment machine does not eliminate single dialyzer modalities. Instead, the blood treatment machine 100 eliminate dual dialyzer modalities (step 1420).

The blood treatment machine 100 then presents bloodline setup (step 1422), the operator would install arterial bloodline 170 into blood pump 202 which would engage sensor 204. The detection of arterial bloodline 170 would result in the initiation of a configurable timer that would count down as user interface 120 displays additional instructions that would be provided by the operator to install dialyzer 140 and venous bloodline 195.

The blood treatment machine 100 then presents instructions for OFFLINE priming reflective of the operator actions taken in decision steps 1406, 1408, 1410, and 1312. In this example, only the hemodialysis (HD) treatment modality would remain. Furthermore, the blood treatment system 100 determines that saline priming will be used since a substitution fluid tubing was not installed into the substitution fluid pump. A similar determination would be made if a substitution fluid pump was not installed on blood treatment machine 100. Additionally, since a substitution fluid line is not used (based on step 1406), there would be no corresponding message on user interface 130 regarding the user of a second substitution fluid pump, even if it were installed on the blood treatment machine 100. Instead, the blood treatment machine 100 presents instructions for saline priming of the extracorporeal blood circuit (step 1412), saline priming is then performed (step 1424), and then the blood treatment machine 100 determines the modality as an HD modality (step 1414).

While certain examples have been described, other examples are possible. For example, depending on the actions of the user in decision steps 1408 and 1410, all of the following treatment modalities with the appropriate preparation steps would be possible: single-needle hemodialysis, and hemodialysis with two dialyzers.

While the extracorporeal blood module 120 is described as having a substitute fluid line connected to the venous line 195 during blood treatment (representing a post-dilution modality), other connections are possible. For example, the substitute fluid line can be connected to the arterial fluid line 170 instead (representing a pre-dilution modality), or in the case of two dialyzers on the blood tubing connected between the first and second dialyzer (representing a mid-dilution modality).

While the extracorporeal blood module 120 has a substitute pump 206, some extracorporeal blood modules do not include a substitute pump 206.

While the extracorporeal blood module 120 has a single-needle pump 208, some extracorporeal blood modules does not include a single-needle pump. For example, some extracorporeal blood modules include a second substitute pump in place of a single-needle pump. In this case, the second substitute pump is similar to substitute pump 206. Both substitute pumps can be electrically connected to the processor of the blood treatment machine.

While the blood treatment machine 100 includes a list of modalities that includes hemodialysis (HD), hemofiltration (HF), hemodiafiltration (HDF), mixed HDF/HD, mid-dilution, pre-dilution, post-dilution, single-needle, and dual-needle modalities, other modalities can be used in other blood treatment machines.

While the blood treatment machine 100 is shown to be configured for a single dialyzer, if the blood treatment machine 100 included the necessary hardware to support a second dialyzer, upon confirmation that a second dialyzer was not desired for the intended treatment modality, an engagement checker would be initiated to monitor the removal of the secondary set of dialysate lines from their respective shunt indicative of their attachment to a second dialyzer. If removal of the second set of dialysate lines occurs, the operator would be returned to decision step 1410 where the operator will affirm that two dialyzers are desired or alternatively return the second set of dialysate lines to their respective shunt.

While the blood treatment system 10 discussed above has been described as including a disposable set with two dialyzers and one substitution fluid line installed, other arrangements are possible. In some embodiments, for example, the blood treatment system can include a disposable set including two dialyzers and two substitution fluid lines installed.

In some examples, the blood treatment machine detects the correct placement of the substitution fluid lines as indicated by the user via user interface 130 (e.g., via arterial pressure unit 214, venous pressure port 240, and optionally pressure sensors between two dialyzers). For example, referring back to FIG. 2A, the blood treatment machine 100 can generate a bolus using the substitution fluid pump 206 before beginning treatment with the venous clamp 228 closed. The venous pressure transducer and the transmembrane pressure sensors of the dialyzer can measure an increased pressure as a result of the bolus. The blood treatment machine can analyze the pressure information related to the bolus to determine any or all of the following: 1) The time in milliseconds that it takes for the bolus to begin to increase the measured venous pressure and transmembrane pressure, 2) the hysteresis or variability with respect to the maximum recorded pressures, 3) The difference between the starting and maximum venous pressure recorded, and 4) The time spent at the maximum venous pressure.

In some examples, pressure change can indicate whether the substitution fluid line is properly installed. In a predilution modality, the bolus is introduced farther away from the venous pressure transducer and would first result in an increase of transmembrane pressure. This increase in pressure causes an overall change in pressure to be smaller than in a post-dilution framework with respect to venous pressure. Furthermore, the time for a venous pressure change to be recorded is larger, the variation between the maximum venous pressure value and end venous pressure value would be less, and the time spent at the maximum pressure value will be of a longer duration. Conversely, in a post-dilution modality, the time for a venous pressure increase to occur is a minimum as the bolus is injected closer to the venous pressure transducer. This means that any transmembrane pressure increase is observed after a venous pressure increase and the variation between the maximum venous pressure and end venous pressure results from a greater hysteresis-effect on the venous pressure caused by the introduction of the bolus. The blood treatment machines described herein can determine whether the blood treatment machines is configured for a pre-dilution modality or a post-dilution modality based on this pressure change. Referring back to FIG. 3B, the testing of a correct substitution fluid line is performed in steps 386 and 387. Referring back to FIG. 9B, the testing of a correct substitution fluid line when two dialyzers and one substitution fluid line is used is performed in steps 934, 935 and 936. Referring back to FIG. 11B, the testing of a correct substitution fluid line when two dialyzers and two substitution fluid lines are used is performed in step 1126. Referring back to FIG. 13B, the testing of a correct substitution fluid line when a single-needle pump is used is performed in steps 1330 and 1331.

In the case of where two dialyzers were connected, a bolus injected before the first dialyzer would take even longer to reach the venous pressure port 240, and the expected increase would be less than if only one dialyzer was connected to blood treatment machine 100. Additionally, there is also the scenario where the bolus would be introduced between a first and second dialyzer. In an optional embodiment where the pressure of the bloodline between the first and second dialyzer is monitored, a bolus injected between a first and second dialyzer would be first detected by an increase in pressure in said line, followed by an increase in transmembrane pressure, followed by an increase in venous pressure. Nevertheless, when two dialyzers are connected and a bolus is injected pre-dilution, an increase in transmembrane pressure and venous pressure would be delayed when compared to a bolus injected between a first and second dialyzer.

In an optional embodiment where transmembrane pressure is independently measured in both dialyzers, a bolus injection between a first and second dialyzer would result in the transmembrane pressures of each dialyzer increasing at roughly the same time, whereas a bolus injection before the first dialyzer would result in an increase in transmembrane pressure first observed in the first dialyzer followed by a smaller increase in pressure observed in the second dialyzer. In the case of both a mid-dilution or pre-dilution bolus injection, independent of whether the first and second dialyzer transmembrane pressures are independently monitored, any observed increase in transmembrane pressure would occur before an observed increase in venous pressure. Accordingly, a bolus injection performed prior to pre-circulation (where blood begins to be pulled from the patient) would allow for a reliable confirmation of the correct placement of a substitution fluid line. Referring back to FIG. 9B, the testing of a correct substitution fluid line when two dialyzers are installed is performed in step 934.

In a similar manner, when a second substitution fluid pump is used a second bolus could be generated upon confirmation of correct placement of the substitution fluid line associated with the first substitution fluid pump. Using the same methodology of analyzing transmembrane pressure and venous pressure, the correct placement of the second substitution fluid line could also be determined. Referring back to FIG. 11B, the testing of the correct placement of substitution fluid line 1 and substitution fluid line 2 is performed in step 1126. The correct placement of a substitution fluid line is not included in FIG. 14 as a substitution fluid line is not installed and/or a substitution fluid pump is not installed on treatment machine 100.

Whenever a treatment modality is determined as described herein, upon entry into treatment mode, the operator may desire to switch the treatment from a current treatment mode to a new treatment mode. Depending on the installed hardware detected by blood treatment machine 100, the user would be allowed to: 1) move from a dual-needle treatment modality to a single-needle treatment modality, 2) move from a hemodialysis treatment modality to a HDF/HF treatment modality, 3) move from a treatment modality using a single substitution fluid pump to a treatment modality using a first and second substitution fluid pump, 4) move from a treatment modality using a single dialyzer to a treatment modality using two dialyzers, 5) move from a treatment modality using two dialyzers to a treatment modality using a single dialyzer, 6) move from a treatment modality using two substitution fluid pumps to a treatment using one or no substitution fluid pumps, 7) move from a HDF/HF treatment modality to an OFFLINE or ONLINE hemodialysis treatment modality, 8) move from a single-needle treatment modality to a dual-needle treatment modality, 9) move from any HDF treatment modality to an HF treatment modality, and 10) move from one HDF or HF treatment to another where the location of a first and/or second substitution fluid line connection is adjusted. Referring back to FIGS. 3A and 3B, FIGS. 9A and 9B, FIGS. 11A and 11B, FIGS. 13A and 13B, and FIG. 14, a transition from a current treatment mode to a newly selected treatment mode would result in re-entry into an associated decision step based on the disposables being added, removed, or adjusted. In a first example, the current treatment mode is a post-dilution HDF modality, corresponding to step 390 in FIG. 3A.

If it were desired to move from a post-dilution HDF modality to a post-dilution HF modality, the blood treatment machine 100 would effectively return to the end of step 388 of FIG. 3B but with the assumption that instead of confirmation button 604 being selected confirmation 606 had instead been selected. The result would be the automatic entry into step 392 and the re-entry into treatment mode in a post-dilution HF modality.

If it were instead desired to switch from a post-dilution HDF modality to a pre-dilution HDF modality, the blood treatment machine would effectively return to decision step 384 of FIG. 3B, but with the assumption that only the pre-dilution information of message 502 would be of relevance and that the post-dilution confirmation button 510 would not be needed as it is the current treatment modality. Upon selection of confirmation button 508 to confirm adjustment from a post-dilution to a pre-dilution configuration, a bolus injection step 386 would not be performed due to the presence of blood in the system, and upon entry into decision step 394 an HDF modality would be automatically assumed resulting in step 396 being reached and the system re-entering treatment mode in a pre-dilution HDF treatment modality (step 396). Upon initiation of the substitution fluid pump for treatment, the same methodology associated with the bolus injection pressure test step 386 could be utilized to detect the appropriate configuration of the substitution fluid line and generate a warning or information message to the operator in the event it was detected that the substitution may not be properly installed in a pre-dilution configuration.

In a more complicated example, if it were desired to switch from single-needle post-dilution HDF modality to a dual-needle pre-dilution HF modality, the blood treatment machine would effectively return to decision step 1308 of FIG. 13A, but with the caveat that the single-needle blood tubing would need to be removed as decision step 1308 is upstream of step 1314 where the single-needle bloodline is primed. In this case, the single-needle blood tubing (and depending on the disposable fluid line in addition to the arterial blood tubing) would need to be removed. Firstly, the blood in the single-needle bloodline would need to be removed to prevent blood loss from the patient. To achieve this in the safest manner a reinfusion process would be performed. Depending on the previous selection in decision step 1306, this reinfusion could be performed in either an ONLINE or OFFLINE manner. For example, if a substitution fluid line was installed in step 1306, the single-needle blood tubing would be disconnected from the patient, the substitution fluid line would be connected to the single-needle blood tubing, and the substitution fluid would introduce a known volume of fluid to displace the blood in the single-needle blood tubing and minimize the introduction of fluid into the dialyzer and venous bloodline. If the blood tubing volume was not known, fluid could be introduced until blood was no longer detected by the machines optical detector associated with the venous blood tubing; however, this would introduce a larger (and potentially unknown) amount of fluid volume. At this point, the single-needle blood tubing would be removed and replaced with a dual-needle arterial bloodline. It would also be necessary to include one (if the first fistula needle was maintained) or two fistula needles into the patient.

Based on the newly established blood treatment machine and disposable configuration, this would represent step 378 of FIG. 3A, and instructions for online priming would be generated with an update of the displayed extracorporeal blood module to reflect the removal of the single-needle blood tubing disposable. Because a venous line and dialyzer would still ostensibly filled with blood, priming would be needed for only the newly installed arterial bloodline. Based on step 354, this would be performed in an ONLINE manner where a known volume of fluid would be introduced into the arterial bloodline; however, priming could equally be achieved in an offline manner with saline. At this point, step 380 would be entered and automatically exited based on the desire to maintain an HDF/HF treatment modality in the newly selected treatment, priming of the arterial bloodline would occur (step 382) with the newly established and primed arterial line being attached to the dialyzer. Since only the arterial line would be primed, a specialized rinse connector with a male luer-lock connection would be used to allow for priming of only the newly installed arterial line while the other blood-filled elements of the extracorporeal blood circuit would remain intact. In this way, the blood treatment machine 100 is configured to prime an arterial fluid line without priming the venous fluid line and/or the dialyzer. Step 384 would be then entered, and based on the desire to change from a post-dilution treatment modality to a pre-dilution treatment modality message box 502 of FIG. 5 would be again displayed, but with the removal of the associated instructions regarding the installation of the substitution fluid line in a post-dilution treatment modality in addition to the removal of post-dilution confirmation button 510. Upon confirmation of the proper setup of the pre-dilution treatment modality, step 394 would be entered and automatically exited based on the desired of an HF treatment modality. Upon exiting step 394, the final treatment modality of a dual-needle pre-dilution HF treatment modality would be confirmed (step 398) and treatment would resume. Step 386 would be skipped based on the presence of blood in the dialyzer and venous bloodline; however, upon initiation of the substitution fluid pump for treatment, the same methodology associated with the bolus injection pressure test step 386 could be utilized to detect the appropriate configuration of the substitution fluid line during treatment and generate a warning or information message to the operator in the event it was detected that the substitution may not be properly installed in a pre-dilution configuration.

In a further example, if it were desired to move from a HD treatment modality to a HD treatment modality using two dialyzers, the blood treatment machine would effectively return to step 1410. Due to the presence of blood in the extracorporeal blood circuit, the operator would be instructed to only prime (using gravity with saline based on step 1406) the newly introduced disposables: 1) the second dialyzer, and 2) the blood tubing intended to connect between the first and second dialyzer which would be attached to the second dialyzer.

It should be noted that priming of a second dialyzer by gravity may not be desirable as it would be difficult to effectively remove all of the air within the dialyzer without the ability to leverage the arterial blood pump, and in some embodiments the transition from a treatment mode requiring one dialyzer to one requiring two dialyzers would only be allowed if online priming could be performed. In the case of online priming, the substitution fluid line would be attached to the blood tubing intended to connect between the first and second dialyzer via a specialized connector with a male luer-lock and female luer-lock and the end of the second dialyzer would be connected to a disposable tubing with a female luer-lock on one end and a rinse port connector on the other. A second set of dialysate lines would be attached to the second dialyzer, and online priming would be performed.

In this offline priming example, the second set of dialysate lines would be attached to the dialyzer, and in step 1412 the second dialyzer would be primed using saline. Upon completion of priming, the venous bloodline would be removed from the first dialyzer and attached to the second dialyzer, the primed bloodline attached to the second dialyzer would be attached to the first dialyzer, and at this point an HD treatment modality would be reconfirmed (step 1414) resulting into the re-entry into treatment.

In each of the listed scenarios, upon indication by the operator that a new treatment mode was desired, the treatment would be paused and some form of a preparation mode would again be entered on user interface 130. Based on the current and newly selected treatment modality, the operator would be instructed to install and remove additional components as required, and upon completion of the preparation steps would again be returned to the treatment mode in the newly requested treatment modality. In so doing, only treatment modes available based on the hardware installed on blood treatment machine 100 would be selectable, and the ability to transfer from one treatment mode to another would be achieved in as simple of a manner as possible.

It should be noted that despite the fact that all of the proposed treatment mode transitions as disclosed herein are possible, they may however not be desirable in a preferred embodiment. For example, transitioning from a single-needle treatment modality to a dual-needle treatment modality may not be desirable as it could represent a contraindication because single-needle treatments are commonly recommended for a patient with a non-mature access (fistula) or in a small access. Moreover, as described above, a transition from a treatment using one dialyzer to a treatment using two dialyzers without online priming ability may also not be desirable due to the inability to leverage an arterial blood pump or substitution fluid pump. Accordingly, in an embodiment certain transitions between a current and newly desired treatment mode could be disabled through a machine service mode setting.

In addition to a transition from a current treatment mode to a newly selected treatment mode, during treatment it may be the case that a tubing line requires replacement as a result of a fluid leak. It may additionally be the case that a dialyzer requires replacement during treatment resultant of the blood treatment machine detecting a blood leak resultant of a broken dialyzer fiber. In these cases, like in the case of transitioning between a current and newly selected treatment mode, upon confirmation of the desire to replace a disposable element, entry into a decision step of figures FIGS. 3A and 3B, FIGS. 9A and 9B, FIGS. 11A and 11B, FIGS. 13A and 13B, and FIG. 14 corresponding to the to be replaced element would occur. These elements would need to be accordingly primed, and reincorporated into the extracorporeal blood circuit, at which point treatment would resume. As described in more detail below, in some examples, specialized connectors are used to prime the newly introduced disposables.

If it were desired to replace an arterial bloodline, venous bloodline, a dialyzer, or a single-needle bloodline in an ONLINE manner, specialized adapter pieces could be used that possess a male luer-lock connector. To minimize the introduction of substitution fluid back into the patient, the to be removed bloodline or dialyzer would be connected to the substitution fluid line, and a known volume would be introduced to displace the blood within the to be removed bloodline or dialyzer. In the case of a venous line or tubing connected between a first and second dialyzer, a specialized connector with a male luer-lock and female luer-lock would be used to connect to the substitution fluid line. The dialyzer outlet would be capped during this time to minimize air exposure. Upon displacement of the blood, the line to be removed would be replaced with a new line that would require priming and reincorporation into the extracorporeal blood circuit.

In the case of the replacement of an arterial or single-needle bloodline, after blood was displaced from the to be replaced line, a specialized rinse connector with a male luer-lock connection would be used to allow only the newly installed line to be primed while the other blood-filled elements of the extracorporeal blood circuit would remain intact. The inlet of the dialyzer would be capped during this time to minimize air exposure.

In the case of the replacement of a dialyzer, a specialized connector with a female luer-lock and female luer-lock would be used to connect the substitution fluid line to the blood entry port of the dialyzer, and a blood tubing line with a female luer-lock to connect to the blood exit port of the dialyzer with an associated rinse connector would be used to allow for online priming. The arterial line and venous line would be temporarily connected together using a specialized male luer-lock to male luer-lock connector.

Upon priming of the newly installed arterial bloodline, single-needle bloodline, dialyzer, or venous bloodline, based on the known volume of fluid introduced by the substitution fluid pump equal to the volume within the newly installed line, upon re-entry into treatment this volume could be removed over the course of treatment by an increase of the ultrafiltration rate.

If the blood treatment machine was incapable of generating online substitution fluid, the use of a saline bag could also achieve the goal of displacing blood in an arterial or single-needle bloodline before removal through gravity and activating the arterial blood pump, as well as for priming of the newly introduced line. Moreover, the OFFLINE priming of said line would again result in a potentially known volume of fluid being introduced into the newly installed arterial or single-needle bloodline (based on the known volume of the disposable or the known rate of the arterial blood pump during priming), and accordingly upon reentry into treatment said volume could be slowly removed from the patient over the course of treatment by an increase of the ultrafiltration rate.

In an example, if it were desired to replace a first or second dialyzer during a post-dilution HDF treatment using two dialyzers resultant of a broken fiber causing the machine to generate a blood leak alarm, the blood treatment machine would effectively return to decision step 910. The dialysate lines associated with the corrupted dialyzer would be returned to their respective shunt, and the operator would be given the option to reconfirm the desire of a treatment using two dialyzers, or to adjust the treatment mode to that of a treatment requiring only a single dialyzer. If it were desired to remove a corrupted first dialyzer and proceed with a HDF treatment using only one dialyzer, the arterial bloodline would be removed from the first dialyzer and attached to either the second dialyzer (with the blood tubing connecting the first and second dialyzer being discarded) or to the blood tubing that had originally connected the first and second dialyzer using a specialized connector with a male luer-lock to male luer-lock. Upon confirmation that only one dialyzer was desired, the treatment would be reinitiated. If it were desired to remove a corrupted second dialyzer and proceed with a HDF treatment using only one dialyzer, the venous bloodline would be removed from the second dialyzer and attached to either the first dialyzer (with the blood tubing connecting the first and second dialyzer being discarded) or to the blood tubing that had originally connected the first and second dialyzer using a specialized connector with a male luer-lock to male luer-lock. Upon confirmation that only one dialyzer was desired, the treatment would be reinitiated.

In some embodiments an attempt to recover the blood in the dialyzer would be made before removal of the corrupted dialyzer. If it were desired to remove a first dialyzer, in a first step the substitution fluid line (present based on decision step 906) would be attached to the first dialyzer using a specialized female luer-lock to female luer-lock adapter and the substitution fluid pump would then introduce a known volume of substitution fluid such that the first dialyzer no longer contained blood (or such that the first dialyzer and blood tubing connecting the first and second dialyzer no longer contained blood if the removal of the blood tubing connecting the first and second dialyzer was desired). During this time a male luer-lock cap would be placed on the end of the arterial bloodline to ensure it was not exposed to air. The first dialyzer would be removed, and the arterial bloodline would be attached to either the second dialyzer (with the blood tubing connecting the first and second dialyzer being discarded) or to the blood tubing that had originally connected the first and second dialyzer using a specialized connector with a male luer-lock to male luer-lock. Upon confirmation that only one dialyzer was desired, the treatment would be reinitiated.

If it were desired to remove a second dialyzer, in a first step the substitution fluid line (present based on decision step 906) would be attached to the blood tubing connecting the first and second dialyzer using a specialized connector with a male luer-lock and female luer-lock, and the substitution fluid pump would introduce a known volume of substitution fluid such that the blood tubing between the first and second dialyzer and the second dialyzer no longer contained blood. During this time the first dialyzer would be capped to ensure it was not exposed to air. Alternatively, the substitution fluid line (present based on decision step 906) would be attached to the second dialyzer using a specialized connector with a female luer-lock to female luer-lock, and the substitution fluid pump would introduce a known volume of substitution fluid such that the second dialyzer no longer contained blood. During this time the blood tubing that had been connected between the first and second dialyzer would have a male luer-lock cap installed to ensure it was not exposed to air.

The second dialyzer would be removed, and the venous bloodline would be removed from the second dialyzer and attached to either the first dialyzer (with the blood tubing connecting the first and second dialyzer being discarded) or the blood tubing that had originally connected the first and second dialyzer using a specialized connector with a male luer-lock to male luer-lock. Upon confirmation that only one dialyzer was desired, the treatment would be reinitiated. In some embodiments, over the course of treatment the fluid volume introduced into the tubing that had originally connected the first and second dialyzer would be removed by increasing the ultrafiltration rate based on the approximately known volume of fluid introduced prior to removing the second dialyzer.

If it were desired to maintain the treatment with two dialyzers, in a first step the substitution fluid line (present based on decision step 906) would be attached to the either the first or second dialyzer using a specialized connector with a female luer-lock to female luer-lock to displace blood in the to be replaced dialyzer. During this time either the arterial blood line or the blood tubing originally connecting the first and second dialyzer would have a male luer-lock cap installed to minimize air exposure. The corrupted dialyzer would be removed and replaced with a new dialyzer, and the system would move to step 914. In this example, since only the dialyzer is to be primed, a rinse connector with blood tubing and a female luer-lock would connect to the blood exit port of the dialyzer, and priming of the dialyzer would occur. During this time the arterial line would be connected to the blood tubing connecting the first and second dialyzer in the case of a replacement of the first dialyzer, or the venous line would be connected to the blood tubing connecting the first and second dialyzer in the case of replacement of the second dialyzer to minimize air exposure. Steps 916 and 917 are skipped as no treatment mode change is occurring, and the system begins online priming of the replacement dialyzer (step 942). Upon completion of priming of the replacement dialyzer, the primed dialyzer would be incorporated into the blood circuit and the system would then move to decision step 918 and message box 1002 of FIG. 10 would be displayed except that instructions of message box 1002 would reflect only the to be maintained filtration modality. Upon selection of confirmation button 1008, blood treatment machine would skip the subsequent pressure check due to the presence of blood in the system, and reconfirm treatment with two dialyzers and re-enter treatment. Upon reentry into treatment, the dialyzer volume could be slowly removed from the patient over the course of treatment by an increase of the ultrafiltration rate.

It should be noted that despite the fact both removal of a first or second dialyzer with an attempt to minimize blood loss and replacement of a first or second dialyzer to maintain a treatment with two dialyzers as disclosed herein may be possible, it may however not be desirable in a preferred embodiment. Depending on the gravity of the blood leak, it may not be advisable to attempt to minimize blood loss before removal of a corrupted first or second dialyzer or return the blood to the patient before replacement of a corrupted first or second dialyzer. Accordingly, in an embodiment of the blood treatment machine service mode setting would only allow removal of a corrupted first or second dialyzer.

What is claimed is:

1. A blood treatment system comprising:

a blood treatment machine comprising a substitution pump and corresponding fluid line, and a further component;

a user interface;

a first sensor configured to detect a presence or an absence of the substitution pump and corresponding fluid line of the blood treatment machine;

a second sensor configured to detect a presence or an absence of the further component of the blood treatment machine;

a processor in communication with the user interface and the first and second sensors, the processor being configured to perform operations comprising:

receiving, from the first sensor, information associated with the presence or the absence of the substitution pump and corresponding fluid line and determining whether the substitution pump and corresponding fluid line are installed in the blood treatment machine;

if the substitution pump and corresponding fluid line are determined not to be installed in the blood treatment machine, eliminating from a set of instructions at least one instruction pertaining to an online modality requiring the substitution pump and corresponding fluid line, and if the substitution pump and corresponding fluid line are determined to be installed in the blood treatment machine, eliminating from the set of instructions at least one instruction pertaining to an offline modality not requiring the substitution pump and corresponding fluid line;

receiving, from the second sensor, information associated with the presence or the absence of the further component and determining whether the further component is installed in the blood treatment machine;

if the further component is determined not to be installed in the blood treatment machine, eliminating from the set of instructions at least one instruction pertaining to a modality requiring the further component, and if the further component is determined to be installed in the blood treatment machine, eliminating from the set of instructions at least one instruction pertaining to a modality not requiring the further component; and presenting the set of instructions on the user interface, wherein the set of instructions pertains to a plurality of possible modalities, wherein the plurality of possible modalities includes hemodialysis (HD), hemofiltration (HF), and hemodiafiltration (HDF).

2. The blood treatment system of claim 1, wherein the set of instructions are for assisting a user in installing at least one of the substitution pump and corresponding fluid line or the further component on the blood treatment machine.

3. The blood treatment system of claim 1, wherein presenting the set of instructions on the user interface comprises presenting an image representing at least one of the substitution pump and corresponding fluid line or the further component being installed on the blood treatment machine.

4. The blood treatment system of claim 1, wherein at least one of the substitution pump and corresponding fluid line is disposable.

5. The blood treatment system of claim 4, wherein the corresponding fluid line is disposable.

6. The blood treatment system of claim 1, wherein the further component comprises a disposable component, wherein the disposable component is a dialyzer.

7. The blood treatment system of claim 1, further comprising receiving information regarding whether the substitution pump and corresponding fluid line and the further component are needed for a particular modality of the set of modalities.

8. The blood treatment system of claim 7, further comprising receiving user input via the user interface.

9. The blood treatment system of claim 1, wherein eliminating from the set of instructions the at least one instruction pertaining to the modality requiring the further component comprises eliminating from the set of instructions at least one instruction pertaining to single-needle modalities when the further component is a single-needle pump and the single-needle pump is determined not to be installed on the blood treatment machine.

10. The blood treatment system of claim 1, wherein eliminating from the set of instructions the at least one instruction pertaining to the modality requiring the further component comprises eliminating from the set of instructions at least one instruction pertaining to dual-needle modalities when the further component is a single-needle pump and the single-needle pump is determined to be installed on the blood treatment machine with a single-needle fluid line attached to the single-needle pump.

11. The blood treatment system of claim 1, wherein eliminating from the set of instructions the at least one instruction pertaining to the modality requiring the further component comprises eliminating from the set of instructions at least one instruction pertaining to single-needle modalities when the further component is a single-needle pump and the single-needle pump is determined to be installed on the blood treatment machine and a single-needle fluid line is not attached to the single-needle pump.

12. The blood treatment system of claim 1, wherein eliminating from the set of instructions the at least one instruction pertaining to the online modality comprises eliminating from the set of instructions at least one instruction pertaining to filtration modalities.

13. The blood treatment system of claim 1, wherein eliminating from the set of instructions the at least one instruction pertaining to the modality requiring the further component comprises eliminating from the set of instructions at least one instruction pertaining to modalities requiring a second dialyzer when the further component is a second set of dialysate lines with an associated shunt and the second set of dialysate lines with the associated shunt is determined not to be installed on the blood treatment machine.

14. The blood treatment system of claim 1, wherein eliminating from the set of instructions the at least one instruction pertaining to the modality requiring the further component comprises eliminating from the set of instructions at least one instruction pertaining to modalities requiring a second dialyzer when the further component is a second set of dialysate lines with an associated shunt and the second set of dialysate lines with the associated shunt is determined to be installed on the blood treatment machine and the second set of dialysate lines remain on the associated shunt.

15. The blood treatment system of claim 1, wherein eliminating from the set of instructions the at least one instruction pertaining to the online modality requiring the substitution pump and corresponding fluid line comprises eliminating from the set of instructions at least one instruction pertaining to pre-dilution filtration modalities, post-dilution filtration modalities, mid-dilution filtration modalities, or a combination thereof.

16. The blood treatment system of claim 1, wherein eliminating from the set of instructions the at least one instruction pertaining to the offline modality comprises eliminating from the set of instructions at least one instruction pertaining to hemodialysis (HD) modalities.

17. The blood treatment system of claim 1, wherein eliminating from the set of instructions the at least one instruction pertaining to the online modality comprises eliminating from the set of instructions at least one instruction pertaining to hemodiafiltration (HDF) or hemofiltration (HF) modalities.

18. A method comprising;

receiving, from a first sensor of a blood treatment machine, information associated with a presence or an absence of a substitution pump and corresponding fluid line of the blood treatment machine, and determining whether the substitution pump and corresponding fluid line is installed in the blood treatment machine;

if the is substitution pump and corresponding fluid line are determined not to be installed in the blood treatment machine, eliminating from a set of instructions at least one instruction pertaining to an online modality requiring the substitution pump and corresponding fluid line, and if the is substitution pump and corresponding fluid line is determined to be installed in the blood treatment machine, eliminating from the set of instructions at least one instruction pertaining to an offline modality not requiring the substitution pump and corresponding fluid line;

receiving, from a second sensor of the blood treatment machine, information associated with a presence or an absence of a further component of the blood treatment machine, and determining whether the further component is installed in the blood treatment machine;

if the further component is determined not to be installed in the blood treatment machine, eliminating from the set of instructions at least one instruction pertaining to a modality requiring the further component, and if the further component is determined to be installed in the blood treatment machine, eliminating from the set of instructions at least one instruction pertaining to a modality not requiring the further component; and presenting the set of instructions on a user interface of the blood treatment machine, wherein the set of instructions pertains to a plurality of possible modalities, wherein the plurality of possible modalities includes hemodialysis (HD), hemofiltration (HF), and hemodiafiltration (HDF).

19. The method of claim 18, wherein the set of instructions are for assisting a user in installing at least one of the substitution pump and corresponding fluid line and the further component on the blood treatment machine.

20. The method of claim 18, wherein presenting the set of instructions on the user interface comprises presenting an image representing at least one of the substitution pump and corresponding fluid line and the further component being installed on the blood treatment machine.

21. The method of claim 18, wherein receiving the information comprises receiving information regarding whether the substitution pump and corresponding fluid line and the further component are needed for a particular modality of the set of modalities.

22. The method of claim 18, further comprising receiving user input via the user interface.

23. The method of claim 18, wherein eliminating from the set of instructions the at least one instruction pertaining to the online modality comprises eliminating from the set of instructions at least one instruction pertaining to filtration modalities.

24. The method of claim 18, wherein at least one of the substitution pump and corresponding fluid line is disposable.

25. The method of claim 24, wherein the corresponding fluid line is disposable.

26. The method of claim 24, wherein the further component is a dialyzer.

27. The method of claim 18, wherein eliminating from the set of instructions the at least one instruction pertaining to the modality requiring the further component comprises eliminating from the set of instructions at least one instruction pertaining to single-needle modalities when the further component is a single-needle pump and the single-needle pump is determined not to be installed on the blood treatment machine.

28. The method of claim 18, wherein eliminating from the set of instructions the at least one instruction pertaining to the modality requiring the further component comprises eliminating from the set of instructions at least one instruction pertaining to dual-needle modalities when the further component is a single-needle pump and the single-needle pump is determined to be installed on the blood treatment machine with a single-needle fluid line attached to the single-needle pump.

29. The method of claim 18, wherein the further component is a reusable component.

30. The method of claim 29, wherein the reusable component is a single-needle blood pump.

31. The method of claim 29, wherein the reusable component is at least one of a set of dialysate lines, a dialyzer line shunt, or a combination thereof.

32. The method of claim 18, wherein first further component comprises at least one of a dialyzer and a fluid line.

33. The method of claim 18, wherein the further component comprises a disposable component and a reusable component.

* * * * *